United States Patent
Yang et al.

(10) Patent No.: US 9,464,145 B2
(45) Date of Patent: Oct. 11, 2016

(54) METALLOCENES AND CATALYST COMPOSITIONS DERIVED THEREFROM

(71) Applicant: ExxonMobil Chemical Patents Inc., Baytown, TX (US)

(72) Inventors: Jian Yang, Houston, TX (US); Xiongdong Lian, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/324,333

(22) Filed: Jul. 7, 2014

(65) Prior Publication Data

US 2015/0025208 A1 Jan. 22, 2015

Related U.S. Application Data

(60) Provisional application No. 61/847,447, filed on Jul. 17, 2013.

(51) Int. Cl.
| | |
|---|---|
| *C07F 17/00* | (2006.01) |
| *C08F 4/6592* | (2006.01) |
| *C08F 10/06* | (2006.01) |
| *C08F 4/76* | (2006.01) |
| *C08F 4/659* | (2006.01) |

(52) U.S. Cl.
CPC ............... *C08F 10/06* (2013.01); *C07F 17/00* (2013.01); *C08F 4/65925* (2013.01); *C08F 4/65927* (2013.01); *C08F 4/76* (2013.01); *C08F 4/65912* (2013.01); *C08F 4/65916* (2013.01)

(58) Field of Classification Search
CPC C07F 17/00; C08F 4/65925; C08F 4/65927; C08F 4/65908; C08F 4/65912; C08F 10/00
See application file for complete search history.

(56) References Cited

U.S. PATENT DOCUMENTS

| | | | |
|---|---|---|---|
| 4,814,540 A | 3/1989 | Watanabe et al. | |
| 5,049,535 A | 9/1991 | Resconi et al. | |
| 5,276,208 A | 1/1994 | Winter et al. | |
| 5,278,264 A | 1/1994 | Spaleck et al. | |
| 5,304,614 A | 4/1994 | Winter et al. | |
| 5,459,117 A | 10/1995 | Ewen | |
| 5,532,396 A | 7/1996 | Winter et al. | |
| 5,543,373 A | 8/1996 | Winter et al. | |
| 5,585,509 A | 12/1996 | Langhauser et al. | |
| 5,631,202 A | 5/1997 | Ewen | |
| 5,677,408 A | 10/1997 | Ueda et al. | |
| 5,696,045 A | 12/1997 | Winter et al. | |
| 5,700,886 A | 12/1997 | Winter et al. | |
| 5,739,366 A | 4/1998 | Imuta et al. | |
| 5,767,033 A | 6/1998 | Imuta et al. | |
| 5,770,753 A | 6/1998 | Küber et al. | |
| 5,786,432 A | 7/1998 | Küber et al. | |
| 5,840,644 A | 11/1998 | Küber et al. | |
| 5,869,584 A | 2/1999 | Winter et al. |
| 6,051,727 A | 4/2000 | Küber et al. |
| 6,057,408 A | 5/2000 | Winter et al. |
| 6,121,182 A | 9/2000 | Okumura et al. |
| 6,136,743 A | 10/2000 | Sugimura et al. |
| 6,150,481 A | 11/2000 | Winter et al. |
| 6,242,544 B1 | 6/2001 | Küber et al. |
| 6,255,506 B1 | 7/2001 | Küber et al. |
| 6,355,819 B1 | 3/2002 | Leino et al. |
| 6,399,533 B2 | 6/2002 | Sacchetti et al. |
| 6,444,833 B1 | 9/2002 | Ewen et al. |
| 6,492,465 B1 | 12/2002 | Burkhardt et al. |
| 6,559,252 B1 | 5/2003 | Horton et al. |
| 6,608,224 B2 | 8/2003 | Resconi et al. |
| 6,635,779 B1 | 10/2003 | Ewen et al. |
| 6,787,618 B1 | 9/2004 | Winter et al. |
| 6,841,501 B2 | 1/2005 | Resconi et al. |
| 6,878,786 B2 | 4/2005 | Resconi et al. |
| 6,949,614 B1 | 9/2005 | Schottek et al. |
| 6,953,829 B2 | 10/2005 | Kratzer et al. |
| 7,034,173 B2 | 4/2006 | Schottek |
| 7,122,498 B2 | 10/2006 | Hart et al. |
| 7,141,527 B1 | 11/2006 | Van Baar et al. |
| 7,220,695 B2 | 5/2007 | Casty et al. |
| 7,314,903 B2 | 1/2008 | Resconi et al. |

(Continued)

FOREIGN PATENT DOCUMENTS

| | | |
|---|---|---|
| CN | 101074276 A | 11/2007 |
| EP | 0 576 970 | 1/1994 |
| EP | 812 854 | 12/1997 |
| EP | 1 209 165 | 5/2002 |
| EP | 1 520 863 | 4/2005 |
| JP | 53-37644 | 4/1978 |
| JP | 55-10599 | 3/1980 |
| JP | 1996-239416 | 9/1996 |
| WO | WO 97/40075 | 10/1997 |
| WO | WO98/46616 | 10/1998 |
| WO | WO00/68279 | 11/2000 |
| WO | WO 01/48034 | 7/2001 |
| WO | WO 02/02575 | 1/2002 |
| WO | WO 02/02576 | 1/2002 |
| WO | WO 03/002583 | 1/2003 |
| WO | WO 03/045551 | 6/2003 |
| WO | WO03/050131 | 6/2003 |
| WO | WO2004/017602 | 2/2004 |
| WO | WO2007/070040 | 6/2007 |
| WO | WO 2008/027116 | 3/2008 |
| WO | WO2010/077230 | 7/2010 |
| WO | WO 2011/051705 | 5/2011 |

OTHER PUBLICATIONS

U.S. Appl. No. 14/324,314, filed Jul. 7, 2014, Yang et al.

(Continued)

*Primary Examiner* — Caixia Lu

(57) ABSTRACT

This invention relates to a novel group 4 transition metal metallocene catalyst compound that is asymmetric having two non-identical indenyl ligands with substitution at $R^2$ having a branched $C_1$-$C_{20}$ alkyl group, $R^8$ having a linear alkyl group and $R^4$ and $R^{10}$ having substituted phenyl groups, where at least one of $R^4$ and $R^{10}$ is a phenyl group substituted at the 3 and 5 position.

38 Claims, No Drawings

(56) References Cited

U.S. PATENT DOCUMENTS

| | | | |
|---|---|---|---|
| 7,342,078 | B2 | 3/2008 | Schottek et al. |
| 7,385,015 | B2 | 6/2008 | Holtcamp |
| 7,405,261 | B2 | 7/2008 | Schulte et al. |
| 7,452,949 | B2 | 11/2008 | Okumura et al. |
| 7,569,651 | B2 | 8/2009 | Schottek et al. |
| 7,615,597 | B2 | 11/2009 | Resconi et al. |
| 7,741,417 | B2 | 6/2010 | Casty et al. |
| 7,799,880 | B2 | 9/2010 | Ciaccia |
| 7,829,495 | B2 | 11/2010 | Floyd et al. |
| 7,964,679 | B2 | 6/2011 | Resconi et al. |
| 7,985,799 | B2 | 7/2011 | Resconi et al. |
| 8,008,653 | B2 | 8/2011 | Lee et al. |
| 8,222,356 | B2 | 7/2012 | Kipke et al. |
| 2002/0019504 | A1 | 2/2002 | Sunaga et al. |
| 2002/0103312 | A1 | 8/2002 | Rausch et al. |
| 2003/0120015 | A1 | 6/2003 | Resconi et al. |
| 2003/0149199 | A1 | 8/2003 | Schottek et al. |
| 2004/0132933 | A1 | 7/2004 | Crowther et al. |
| 2004/0132935 | A1 | 7/2004 | Arjunan et al. |
| 2005/0182266 | A1 | 8/2005 | Schulte et al. |
| 2005/0228155 | A1 | 10/2005 | Kawai et al. |
| 2005/0261449 | A1 | 11/2005 | Voskoboynikov et al. |
| 2006/0116490 | A1 | 6/2006 | Paczkowski et al. |
| 2009/0259007 | A1 | 10/2009 | Ciaccia |
| 2010/0249346 | A1 | 9/2010 | Schiendorfer et al. |
| 2010/0261860 | A1 | 10/2010 | Schulte et al. |
| 2010/0267907 | A1 | 10/2010 | Dimeska et al. |
| 2011/0230630 | A1 | 9/2011 | Sell et al. |
| 2013/0150541 | A1 | 6/2013 | Crowther et al. |

OTHER PUBLICATIONS

Caldwell et al., "*Are Perpendicular Alkene Triplets Just 1,2-Biradicals? Studies with the Cyclopropylcarbinyl Clock*", Journal of the American Chemical Society, Mar. 1994, vol. 116, No. 6, pp. 2271-2275.

Deng et al., "*Nickel-catalyzed Carboannulation Reaction of o-Bromobenzyl Zinc Bromide with Unsaturated Compounds*", Organic Letters, 2007, vol. 9, No. 25, pp. 5207-5210.

de Meijere et al., "*An Efficient Three-Step Synthesis of Cyclpenta[b]pyrans via 2-Donor-Substituted Fischer Ethenylcarbenechromium Complexes*", Chemistry: A European Journal, 2005, Wiley-VCH Verlag GmbH & Co. KGaA, Weinheim, vol. 11, pp. 4132-4148.

Izmer et al., "*Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands*", Journal of Organometallic Chemistry (2005), vol. 690, Issue 4, pp. 1067-1079.

Kaneyoshi, H. et al., "*Synthesis of Block and Graft Copolymers with Linear Polyethylene Segments by Combination of Degenerative Transfer Coordination Polymerization and Atom Transfer Radical Polymerization*," Macromolecules, vol. 38, Issue 13, 2005, pp. 5425-5435.

Mochalov et al., "*Transformations of Arylcyclopropanes Under the Action of Dinitrogen Tetroxide*", Journal of Organic Chemistry of the USSR (Translation of Zhurnal Organicheskoi Khimii) (1998), vol. 34, Issue 9, pp. 1322-1330.

Mochalov et al., "*Nitration of Biphenylcyclopropanes*", Journal of Organic Chemistry of the USSR (Zhurnal Organicheskoi Khimii), May 1976, vol. 12, Issue 5, pp. 1008-1014.

Ransom et al., "*Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands*", Organometallics (2011), vol. 30, Issue 4, pp. 800-814.

Riemschneider et al., "*Chemistry of Polyhalocyclopentadienes and Related Compounds. XVII. Reaction of Hexachlorocyclopentadiene with Unsaturated Compounds*", Monatshefte fuer Chemie, 1960, vol. 91, Issue 1, pp. 22-40. (English language abstract attached.).

Rulhoff et al., "*Synthesis and Characterization of Propylene and Linear Ethylene Oligomers ($C_n$=26-28) with Metallocenes/MAO Catalysts*," Macromolecular Chemistry and Physics, vol. 207, Issue 16, 2006, pp. 1450-1460.

Shabarov et al., "*Reaction of 2-cyclpropylfluorene with Mercury Acetate*", Vestnik Moskovskogo Universiteta, Seriya 2. Khimiya, Moscow University Chemistry Bulletin, 1976, vol. 17, Issue 5, pp. 620-621.

Waugh et al., "*Upper Excited State Photochemistry: Solution and Gas Phase Photochemistry and Photophysics of 2- and 3-Cyclopropylindene[1]*", Journal of the American Chemical Society, Mar. 1999, vol. 121, Issue 13, pp. 3083-3092.

Yoshida, Z., "*Novel Pi Systems Possessing Cyclopropenylidene Moiety*", Pure & Applied Chemistry, vol. 54, No. 5 (1982), pp. 1059-1074.

METALLOCENES AND CATALYST COMPOSITIONS DERIVED THEREFROM

PRIORITY

This application claims the benefit of and priority to U.S. Provisional Application No. 61/847,447, filed Jul. 17, 2013, the disclosure of which is fully incorporated herein by reference.

FIELD OF THE INVENTION

This invention relates to novel catalyst compounds and catalyst systems comprising asymmetric substituted indenyl groups and uses thereof.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization are often based on metallocenes as catalyst precursors, which are activated either with an alumoxane or with an activator containing a non-coordinating anion.

U.S. Pat. No. 7,829,495 discloses alkyl substituted metallocenes having a " . . . $C_3$ or greater hydrocarbyl . . . substitutent bonded to either the $L^A$ or $L^B$ ring through a primary carbon atom . . . preferably an n-alkyl substituent . . . " (see column 4, lines 9-12). Further, in the Examples section, (n-propylcyclopentadienyl)(tetramethylcyclopentadienyl)zirconium dichloride combined with methylalumoxane and Davision™ 948 silica is used for ethylene hexene polymerization; bis(n-propyl cyclopentadienyl) zirconium dichloride combined with methylalumoxane and Davision™ 948 silica is used for ethylene hexene polymerization; and dimethylsilyl(flourenyl)(n-propyl cyclopentadienyl) zirconium dichloride combined with methylalumoxane and Davision silica is used for ethylene hexene polymerization.

Other references of interest include U.S. Pat. No. 6,051,727, U.S. Pat. No. 6,255,506, EP 0 576 970, U.S. Pat. No. 5,459,117, U.S. Pat. No. 5,532,396, U.S. Pat. No. 5,543,373, U.S. Pat. No. 5,585,509, U.S. Pat. No. 5,631,202, U.S. Pat. No. 5,696,045, U.S. Pat. No. 5,700,886, U.S. Pat. No. 6,492,465, U.S. Pat. No. 6,150,481, U.S. Pat. No. 5,770,753, U.S. Pat. No. 5,786,432, U.S. Pat. No. 5,840,644, U.S. Pat. No. 6,242,544, U.S. Pat. No. 5,869,584, U.S. Pat. No. 6,399,533, U.S. Pat. No. 6,444,833, U.S. Pat. No. 6,559,252, U.S. Pat. No. 6,608,224, U.S. Pat. No. 6,635,779, U.S. Pat. No. 6,841,501, U.S. Pat. No. 6,878,786, U.S. Pat. No. 6,949,614, U.S. Pat. No. 6,953,829, U.S. Pat. No. 7,034,173, U.S. Pat. No. 7,141,527, U.S. Pat. No. 7,314,903, U.S. Pat. No. 7,342,078, U.S. Pat. No. 7,405,261, U.S. Pat. No. 7,452,949 U.S. Pat. No. 7,569,651, U.S. Pat. No. 7,615,597, U.S. Pat. No. 7,799,880, U.S. Pat. No. 7,964,679, U.S. Pat. No. 7,985,799, U.S. Pat. No. 8,222,356, U.S. Pat. No. 5,278,264, U.S. Pat. No. 5,276,208, U.S. Pat. No. 5,049,535, US2011/0230630, WO02/002575; WO 02/022576, WO 02/022575, WO 2003/002583, U.S. Pat. No. 7,122,498, US 2011/0230630, US 2010/0267907, EP 1 250 365, WO 97/9740075 and WO 03/045551.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties.

It is therefore an object of the present invention to novel catalyst compounds, catalysts systems comprising such compounds, and processes for the polymerization of olefins using such compounds and systems.

SUMMARY OF THE INVENTION

This invention relates to a metallocene catalyst compound represented by the formulae:

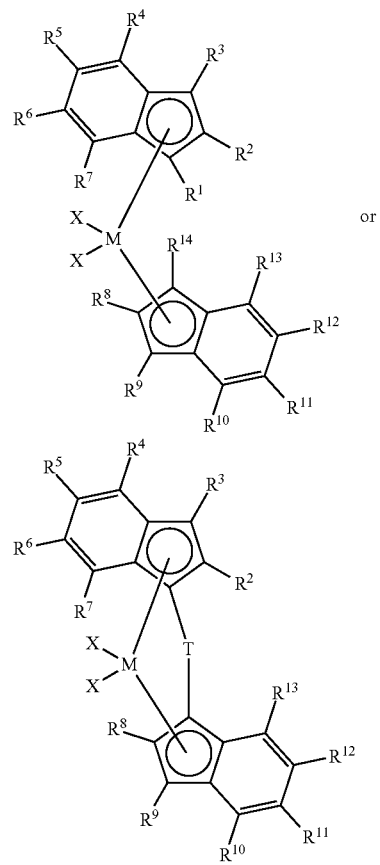

wherein,
$R^2$ and $R^8$ are not the same;
$R^4$ and $R^{10}$ are substituted phenyl groups, where at least one of $R^4$ and $R^{10}$ is a phenyl group substituted at the 3 and 5 position;
M is a group transition 2, 3 or 4 metal;
T is a bridging group;
each X is an anionic leaving group;
each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;
$R^2$ is a substituted or unsubstituted $C_3$-$C_{20}$ hydrocarbyl group, where the group is substituted at the alpha position; and
$R^8$ is a linear $C_1$-$C_{10}$ alkyl group which may be halogenated.

This invention further relates to a catalyst system comprising such metallocenes and an activator.

This invention further relates to a method to polymerize olefins comprising contacting olefins with a catalyst system comprising said metallocene catalyst compound(s) described above and an activator.

DETAILED DESCRIPTION

For the purposes of this invention and the claims thereto, the new numbering scheme for the Periodic Table Groups is used as described in CHEMICAL AND ENGINEERING NEWS, 63(5), p. 27 (1985). Therefore, a "Group 4 metal" is an element from Group 4 of the Periodic Table.

Unless otherwise indicated, "catalyst productivity" is a measure of how many grams of polymer (P) are produced using a polymerization catalyst comprising W g of catalyst (cat), over a period of time of T hours; and may be expressed by the following formula: P/(T×W) and expressed in units of $gPgcat^{-1}\ hr^{-1}$. Unless otherwise indicated, "catalyst activity" is a measure of how active the catalyst is and is reported as the mass of product polymer (P) produced per mole of catalyst (cat) used (kgP/molcat). Unless otherwise indicated, "conversion" is the amount of monomer that is converted to polymer product, and is reported as mol % and is calculated based on the polymer yield and the amount of monomer fed into the reactor.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is typically a polymer having a low molecular weight (such an Mn of less than 25,000 g/mol, preferably less than 2,500 g/mol) or a low number of mer units (such as 75 mer units or less). An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

For purposes of this invention and claims thereto, the term "substituted" means that a hydrogen group has been replaced with a heteroatom or a heteroatom containing group. For example, a "substituted hydrocarbyl" is a radical made of carbon and hydrogen where at least one hydrogen is replaced by a heteroatom or heteroatom containing group.

Unless otherwise indicated, room temperature is 23° C.

"Different" or "not the same" as used to refer to R groups in any formula herein (e.g. R2 and R8 or R4 and R10) or any substituent herein indicates that the groups or substituents differ from each other by at least one atom or are different isomerically.

As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane.

A "catalyst system" is combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group.

"Asymmetric" as used in connection with the instant indenyl compounds means that the substitutions at the 4 positions are different, or the substitutions at the 2 positions are different, or the substitutions at the 4 positions are different and the substitutions at the 2 positions are different.

Metallocene Catalyst Compounds

The invention relates to a metallocene catalyst compound represented by the formula:

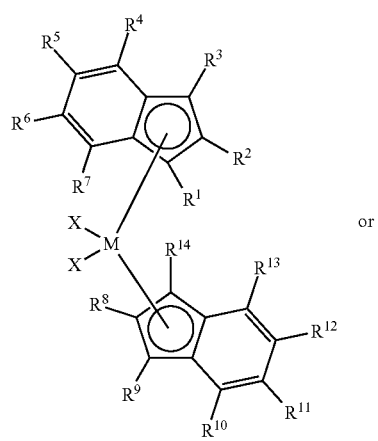

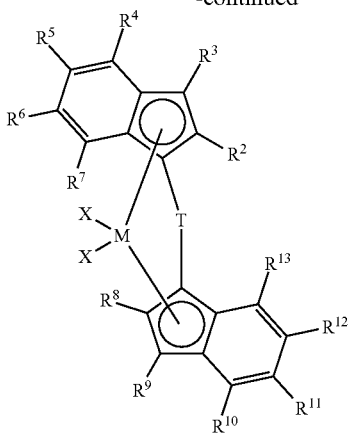

wherein,

R² and R⁸ are not the same;

R⁴ and R¹⁰ are substituted phenyl groups, where at least one of R⁴ and R¹⁰ is a phenyl group substituted at the 3 and 5 position;

M is a group transition 2, 3 or 4 metal;

T is a bridging group;

each X is an anionic leaving group;

each R¹, R³, R⁵, R⁶, R⁷, R⁹, R¹¹, R¹², R¹³, and R¹⁴ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;

R² is a substituted or unsubstituted C₃-C₂₀ hydrocarbyl group, where the group is substituted at the alpha position; and R⁸ is a linear C₁-C₁₀ alkyl group which may be halogenated.

By "substituted phenyl group" is meant a phenyl is substituted with 1, 2, 3, 4 or 5 C₁ to C₂₀ substituted or unsubstituted hydrocarbyl groups, such as methyl, ethyl, propyl, butyl, pentyl, hexyl, heptyl, octyl, nonyl, decyl, undecyl, dodecyl, phenyl, substituted phenyl, biphenyl or an isomer thereof. Preferably the phenyl group is substituted at the meta or para positions, preferably the 3 and/or 5 positions, preferably with C4 to C12 alkyl groups. Alternately the phenyl may be substituted at the 2 position, but is preferably not substituted in the 2 and 6 positions, e.g. in a preferred embodiment if the invention when the 2 position of the phenyl is substituted, the 6 position is H).

In one aspect, R² is an alkyl group which is branched in α-position, preferably R² is an isopropyl, sec-butyl, 1-methylbutyl, 1-ethylpropyl, 1-methylpentyl, 1-ethylbutyl, 1-methylhexyl, 1-ethylpentyl, 1-propylbutyl, etc.

In an aspect R⁸ is a linear C₁-C₁₀ alkyl group, preferably methyl, ethyl, propyl, butyl, pentyl, hexyl, heptyl, octyl, nonyl or decyl) which may be halogenated, preferably with I, F, Cl or Br.

In another aspect, R⁴ and R¹⁰ are independently substituted phenyl groups, preferably phenyl groups substituted with C₁ to a C₁₀ alkyl groups (such as t-butyl, sec-butyl, n-butyl, isopropyl, n-propyl, cyclopropyl, cyclobutyl, cyclopentyl, cyclohexyl, cycloheptyl, cyclooctyl, phenyl, mesityl, or adamantyl), or an aryl group which may be further substituted with an aryl group, and the two aryl groups bound together can be joined together directly or by linker groups, wherein the linker group is an alkyl, vinyl, phenyl, alkynyl, silyl, germyl, amine, ammonium, phosphine, phosphonium, ether, thioether, borane, borate, alane or aluminate groups, provided that here at least one of R⁴ and R¹⁰ is a phenyl group substituted at the 3 and 5 position.

In another aspect, one of one of R⁴ and R¹⁰ is a phenyl group substituted at the 2' position with an aryl group, such as a phenyl group.

In yet another aspect, at least one of R⁴ and R¹⁰ is a phenyl group substituted at the 3 and 5 positions with C₁ to a C₁₀ alkyl groups, such as a tertiary butyl group.

In yet another aspect, both R⁴ and R¹⁰ are a phenyl group substituted at the 3 and 5 positions with C₁ to a C₁₀ alkyl groups, such as a tertiary butyl group.

In still another aspect, at least one of R⁴ and R¹⁰ is a phenyl group substituted at the 3' and 5' positions with aryl groups, such as substituted or unsubstituted phenyl groups.

In still another aspect, both R⁴ and R¹⁰ are a phenyl group substituted at the 3' and 5' positions with aryl groups, such as substituted or unsubstituted phenyl groups.

In another aspect, at least one of R⁴ and R¹⁰ is an aryl group substituted at 3' and 5' positions with C₁ to a C₁₀ alkyl groups (such as t-butyl, sec-butyl, n-butyl, isopropyl, n-propyl, cyclopropyl, cyclobutyl, cyclopentyl, cyclohexyl, cycloheptyl, cyclooctyl, phenyl, mesityl, or adamantyl) or aryl groups and combinations thereof, wherein, when R⁴ or R¹⁰ is a phenyl group which is further substituted with an aryl group, the two groups bound together can be joined together directly or by linker groups, wherein the linker group is an alkyl, vinyl, phenyl, alkynyl, silyl, germyl, amine, ammonium, phosphine, phosphonium, ether, thioether, borane, borate, alane or aluminate groups.

In yet another aspect, M is Hf, Ti and/or Zr, particularly Hf and/or Zr, particularly Zr.

Suitable radicals for the each of the groups R¹, R³, R⁵, R⁶, R⁷, R⁹, R¹¹, R¹², R¹³, and R¹⁴ are selected from hydrogen or hydrocarbyl radicals including methyl, ethyl, ethenyl, and all isomers (including cyclics such as cyclohexyl) of propyl, butyl, pentyl, hexyl, heptyl, octyl, nonyl, decyl, undecyl, dodecyl, propenyl, butenyl, and from halocarbyls and all isomers of halocarbyls including perfluoropropyl, perfluorobutyl, perfluoroethyl, perfluoromethyl, and from substituted hydrocarbyl radicals and all isomers of substituted hydrocarbyl radicals including trimethylsilylpropyl, trimethylsilylmethyl, trimethylsilylethyl, and from phenyl, and all isomers of hydrocarbyl substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, dipropylmethylphenyl, and the like; from all isomers of halo substituted phenyl (where halo is, independently, fluoro, chloro, bromo and iodo) including halophenyl, dihalophenyl, trihalophenyl, tetrahalophenyl, and pentahalophenyl; and from all isomers of halo substituted hydrocarbyl substituted phenyl (where halo is, independently, fluoro, chloro, bromo and iodo) including halomethylphenyl, dihalomethylphenyl, (trifluoromethyl)phenyl, bis (triflouromethyl)phenyl; and from all isomers of benzyl, and all isomers of hydrocarbyl substituted benzyl including methylbenzyl, dimethylbenzyl.

In other embodiments, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system).

Suitable examples for X include chloride, bromide, fluoride, iodide, hydride, and C₁ to C₂₀ hydrocarbyls, preferably methyl, ethyl, propyl, butyl, pentyl, hexyl, phenyl, benzyl, and all isomers thereof, or two X together are selected from $C_4$ to $C_{10}$ dienes, preferably butadiene, methylbutadiene, pentadiene, methylpentadiene, dimethylpentadiene, hexadiene, methylhexadiene, dimethylhexadiene, or from $C_1$ to $C_{10}$ alkylidenes, preferably methylidene, ethylidene, propylidene, or from $C_3$ to $C_{10}$ alkyldiyls, preferably propandiyl, butandiyl, pentandiyl, and hexandiyl. In particular, X is chloride or methyl.

In another embodiment, T is selected from $R'_2C$, $R'_2Si$, $R'_2Ge$, $R'_2CCR'_2$, $R'_2CCR'_2CR'_2$, $R'C=CR'$, $R'C=CR'CR'_2$, $R'_2CSiR'_2$, $R'_2SiSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B$, $R'_2C—BR'$, $R'_2C—BR'—CR'_2$, $R'N$, $R'_2C—NR'$, $R'_2C—NR'—CR'_2$, $R'P$, $R'_2C—PR'$, and $R'_2C—PR'—CR'_2$ where R' is, independently, hydrogen, hydrocarbyl, substituted hydrocarbyl, halocarbyl, substituted halocarbyl, silylcarbyl, or germylcarbyl, and two or more R' on the same atom or on adjacent atoms may join together to form a substituted or unsubstituted, saturated, partially unsaturated, or aromatic cyclic or polycyclic substituent.

Suitable examples for the bridging group T include dihydrocarbylsilylenes including dimethylsilylene, diethylsilylene, dipropylsilylene, dibutylsilylene, dipentylsilylene, dihexylsilylene, methylphenylsilylene, diphenylsilylene, dicyclohexylsilylene, methylcyclohexylsilylene, dibenzylsilylene, tetramethyldisilylene, cyclotrimethylenesilylene, cyclotetramethylenesilylene, cyclopentamethylenesilylene, divinylsilylene, and tetramethyldisiloxylene; dihydrocarbylgermylenes including dimethylgermylene, diethylgermylene, dipropylgermylene, dibutylgermylene, methylphenylgermylene, diphenylgermylene, dicyclohexylgermylene, methylcyclohexylgermylene, cyclotrimethylenegermylene, cyclotetramethylenegermylene, and cyclopentamethylenegermylene; carbylenes and carbdiyls including methylene, dimethylmethylene, diethylmethylene, dibutylmethylene, dipropylmethylene, diphenylmethylene, ditolylmethylene, di(butylphenyl)methylene, di(trimethylsilylphenyl)methylene, dibenzylmethylene, cyclotetramethylenemethylene, cyclopentamethylenemethylene, ethylene, methylethylene, dimethylethylene, trimethylethylene, tetramethylethylene, cyclopropylene, cyclobutylene, cyclopentylene, cyclohexylene, propanediyl, methylpropanediyl, dimethylpropanediyl, trimethylpropanediyl, tetramethylpropanediyl, pentamethylpropanediyl, hexamethylpropanediyl, vinylene, and ethene-1,1-diyl; boranediyls including methylboranediyl, ethylboranediyl, propylboranediyl, butylboranediyl, pentylboranediyl, hexylboranediyl, cyclohexylboranediyl, and phenylboranediyl; and combinations thereof including dimethylsilylmethylene, diphenylsilylmethylene, dimethylsilylethylene, methylphenylsilylmethylene.

In particular, T is $CH_2$, $CH_2CH_2$, $C(CH_3)_2$, $SiMe_2$, $SiPh_2$, SiMePh, $Si(CH_2)_3$, $Si(CH_2)_4$, $Si(Me_3SiPh)_2$, or $Si(CH_2)_5$.

In another embodiment, T is represented by the formula $R_2{}^aJ$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

In a preferred embodiment of the invention in any formula described herein, T is represented by the formula, $(R^*{}_2G)_g$, where each G is C, Si, or Ge, g is 1 or 2, and each $R^*$ is, independently, hydrogen, halogen, C1 to C20 hydrocarbyl or a C1 to C20 substituted hydrocarbyl, and two or more $R^*$ can form a cyclic structure including aromatic, partially saturated, or saturated cyclic or fused ring system.

In particular embodiments, the rac/meso ratio of the metallocene catalyst is 50:1 or greater, or 40:1 or greater, or 30:1 or greater, or 20:1 or greater, or 15:1 or greater, or 10:1 or greater, or 7:1 or greater, or 5:1 or greater.

In an embodiment of the invention, the metallocene catalyst comprises greater than 55 mol % of the racemic isomer, or greater than 60 mol % of the racemic isomer, or greater than 65 mol % of the racemic isomer, or greater than 70 mol % of the racemic isomer, or greater than 75 mol % of the racemic isomer, or greater than 80 mol % of the racemic isomer, or greater than 85 mol % of the racemic isomer, or greater than 90 mol % of the racemic isomer, or greater than 92 mol % of the racemic isomer, or greater than 95 mol % of the racemic isomer, or greater than 98 mol % of the racemic isomer, based on the total amount of the racemic and meso isomer-if any, formed. In a particular embodiment of the invention, the bridged bis(indenyl)metallocene transition metal compound formed consists essentially of the racemic isomer.

Amounts of rac and meso isomers are determined by proton NMR. $^1H$ NMR data are collected at 23° C. in a 5 mm probe using a 400 MHz Bruker spectrometer with deuterated methylene chloride or deuterated benzene. Data is recorded using a maximum pulse width of 45°, 8 seconds between pulses and signal averaging 16 transients. The spectrum is normalized to protonated methylene chloride in the deuterated methylene chloride, which is expected to show a peak at 5.32 ppm.

In a preferred embodiment in any of the processes described herein one catalyst compound is used, e.g. the catalyst compounds are not different. For purposes of this invention one metallocene catalyst compound is considered different from another if they differ by at least one atom. For example "bisindenyl zirconium dichloride" is different from (indenyl)(2-methylindenyl) zirconium dichloride" which is different from "(indenyl)(2-methylindenyl) hafnium dichloride." Catalyst compounds that differ only by isomer are considered the same for purposes if this invention, e.g., rac-dimethylsilylbis(2-methyl 4-phenyl)hafnium dimethyl is considered to be the same as meso-dimethylsilylbis(2-methyl 4-phenyl)hafnium dimethyl.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds should be chosen such that the two are compatible. A simple screening method such as by $^1H$ or $^{13}C$ NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an $X_1$ or $X_2$ ligand which is not a hydride, hydrocarbyl, or substituted hydrocarbyl, then the alumoxane should be contacted with the transition metal compounds prior to addition of the non-coordinating anion activator.

The transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Methods to Prepare the Catalyst Compounds

Generally, metallocenes of this type are synthesized as shown below where (i) is a deprotonation via a metal salt of alkyl anion (e.g. nBuLi) to form an indenide. (ii) reaction of indenide with an appropriate bridging precursor (e.g. Me$_2$SiCl$_2$). (iii) reaction of the above product with AgOTf. (iv) reaction of the above triflate compound with another equivalent of indenide. (v) double deprotonation via an alkyl anion (e.g. nBuLi) to form a dianion (vi) reaction of the dianion with a metal halide (e.g. ZrCl$_4$). The final products are obtained by recrystallization of the crude solids.

generally oligomeric compounds containing —Al(R$^1$)—O— sub-units, where R$^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When the activator is an alumoxane (modified or unmodified), some embodiments select the maximum amount of activator at a 5000-fold molar excess Al/M over the catalyst

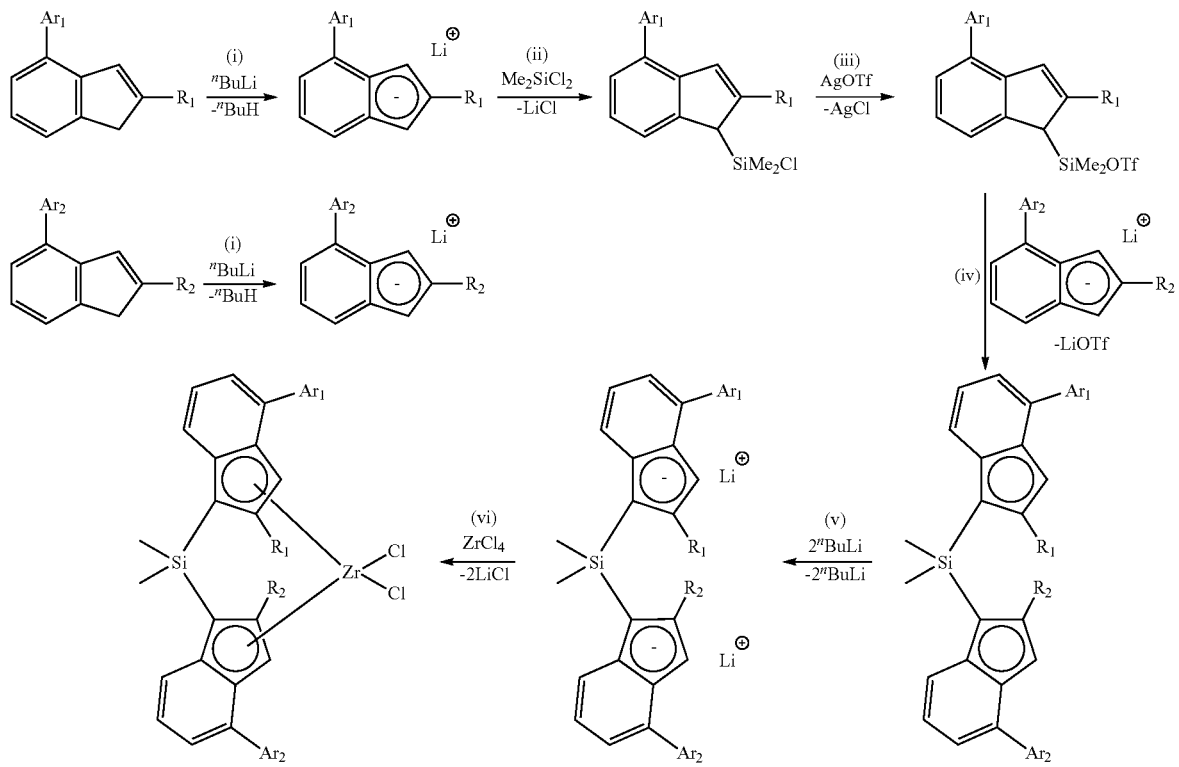

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are compound (per metal catalytic site). The minimum activator-to-catalyst-compound is a 1:1 molar ratio. Alternate preferred ranges include from 1:1 to 1000:1, alternately from 1:1 to 500:1 alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri(n-butyl)ammonium tetrakis(pentafluorophenyl)borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277, 003 A1, and EP 0 277,004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (II):

$$(Z)_d^+(A^{d-}) \qquad (II)$$

wherein Z is (L-H) or a reducible Lewis Acid, L is an neutral Lewis base; H is hydrogen; (L-H)$^+$ is a Bronsted acid; $A^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)$_d^+$ is a Bronsted acid, capable of donating a proton to the transition metal catalytic precursor resulting in a transition metal cation, including ammoniums, oxoniums, phosphoniums, siliyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl. In a preferred embodiment, the reducible Lewis acid is triphenyl carbenium.

The anion component $A^{d-}$ include those having the formula [M$^{k+}$Q$_n$]$^{d-}$ wherein k is 1, 2, or 3; n is 1, 2, 3, 4, 5, or 6, preferably 3, 4, 5 or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene) with an amidinate catalyst compound, a chain transfer agent and a boron containing NCA activator represented by the formula (14):

$$Z_d^+(A^{d-}) \qquad (14)$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d$^-$ (as further described above); d is 1, 2, or 3.

In a preferred embodiment in any NCA's represented by Formula 14 described above, the reducible Lewis acid is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's represented by Formula 14 described above, $Z_d^+$ is represented by the formula: $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

In a preferred embodiment in any of the NCA's represented by Formula 14 described above, the anion component $A^{d-}$ is represented by the formula $[M^{*k*+}Q^*_{n*}]^{d*-}$ wherein k* is 1, 2, or 3; n* is 1, 2, 3, 4, 5, or 6 (preferably 1, 2, 3, or 4); n*–k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene) with an amidinate catalyst compound, a chain transfer agent and an NCA activator represented by the formula (I):

$$R_nM^{**}(ArNHal)_{4-n} \quad (I)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula I also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula I described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; $-SR^1$, $-NR^2_2$, and $-PR^3_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula I described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula I described above, the NCA also comprises a cation represented by the formula, $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (16):

$$(OX^{e+})_d(A^{d-})_e \quad (16)$$

wherein $OX^{e+}$ is a cationic oxidizing agent having a charge of e+; e is 1, 2, or 3; d is 1, 2 or 3; and $A^{d-}$ is a non-coordinating anion having the charge of d– (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis(pentafluorophenyl)borate.

In another embodiment, the catalyst compounds described herein can be used with Bulky activators. A "Bulky activator" as used herein refers to anionic activators represented by the formula:

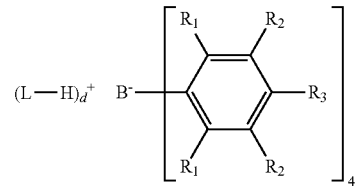

where:
each $R_1$ is, independently, a halide, preferably a fluoride;
each $R_2$ is, independently, a halide, a $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_2$ is a fluoride or a perfluorinated phenyl group); each $R_3$ is a halide, $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is an neutral Lewis base; $(L-H)^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetra-

| Activator | Structure of boron substituents | Molecular Formula of each substituent | $V_S$ | MV Per subst. (Å³) | Total MV (Å³) |
|---|---|---|---|---|---|
| Dimethylanilinium tetrakis(perfluoronaphthyl)borate | 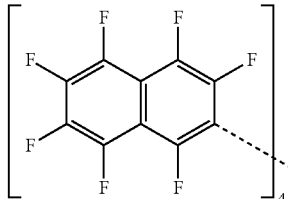 | $C_{10}F_7$ | 34 | 261 | 1044 |
| Dimethylanilinium tetrakis(perfluorobiphenyl)borate | 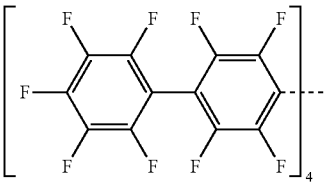 | $C_{12}F_9$ | 42 | 349 | 1396 |
| [4-tButyl-PhNMe₂H] [(C₆F₃(C₆F₅)₂)₄B] | 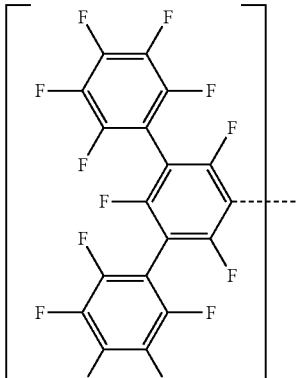 | $C_{18}F_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl) kis(perfluorobiphenyl)borate, [4-t-butyl-PhNMe₂H][(C₆F₃(C₆F₅)₂)₄B], and the types disclosed in U.S. Pat. No. 7,297,653.

Illustrative, but not limiting, examples of boron compounds which may be used as an activator in the processes of this invention are: trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl) ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts, such as: di-(i-propyl) ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium)tetrakis(pentafluorophenyl)borate, trialkylammonium tetrakis-(2,3,4,6-tetrafluorophenyl)borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium)tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

In a preferred embodiment, any of the activators described herein may be mixed together before or after combination with the catalyst compound, preferably before being mixed with the catalyst compound.

In some embodiments two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. No. 5,153,157, U.S. Pat. No. 5,453,410, EP 0 573 120 B1, WO 94/07928, and WO 95/14044 which discuss the use of an alumoxane in combination with an ionizing activator).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON 952 or DAVISON 955 by the Davison Chemical Division of W.R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as propylene), and optionally comonomer, are contacted with a catalyst system comprising an activator and at least one metallocene compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof. In a preferred embodiment of the invention, the monomer comprises propylene and an optional comonomers comprising one or more of ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and an optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes of this invention can be carried out in any manner known in the art. Any suspension, homogeneous, bulk, solution (including supercritical), slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is typically a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In some embodiments hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa). In some embodiments hydrogen is not added the polymerization reactor, i.e. hydrogen may be present from other sources, such as a hydrogen generating catalyst, but none is added to the reactor.

In an embodiment of the invention, the activity of the catalyst is at least 50 g/mmol/hour, preferably 500 g/mmol/hour or more, preferably 5000 g/mmol/hr or more, preferably 50,000 g/mmol/hr or more, preferably 100,000 g/mmol/hr or more, preferably 150,000 g/mmol/hr or more, preferably 200,000 g/mmol/hr or more, preferably 250,000 g/mmol/hr or more, preferably 300,000 g/mmol/hr or more, preferably 350,000 g/mmol/hr or more. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally scavengers (such as trialkyl aluminum compounds) are absent (e.g. present at zero mol %, alternately the scavenger is present at a molar ratio of scavenger metal to transition metal of less than 100:1, preferably less than 50:1, preferably less than 15:1, preferably less than 10:1); and 8) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Gas Phase Polymerization

Generally, in a fluidized gas phase process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. Illustrative gas phase polymerization processes can be as discussed and described in U.S. Pat. Nos. 4,543,399; 4,588,790; 5,028,670; 5,317,036; 5,352,749; 5,405,922; 5,436,304; 5,453,471; 5,462,999; 5,616,661; and 5,668,228.

The reactor pressure in a gas phase process can vary from about 69 kPa to about 3,450 kPa, about 690 kPa to about 3,450 kPa, about 1,380 kPa to about 2,759 kPa, or about 1,724 kPa to about 2,414 kPa.

The reactor temperature in the gas phase process can vary from about 30° C. to about 120° C., preferably from about 60° C. to about 115° C., more preferably in the range of from about 65° C. to about 110° C., and most preferably in the range of from about 70° C. to about 95° C. In another embodiment, when high density polyethylene is desired the reactor temperature is typically between about 70° C. and about 105° C.

The productivity of the catalyst or catalyst system in a gas phase system is influenced by the partial pressure of the main monomer. The preferred mole percent of the main monomer, ethylene or propylene, preferably ethylene, is from about 25 mol % to about 90 mol % and the comonomer partial pressure is from about 138 kPa to about 5,000 kPa, preferably about 517 kPa to about 2,069 kPa, which are typical conditions in a gas phase polymerization process. Also in some systems the presence of comonomer can increase productivity.

In a preferred embodiment, the reactor can be capable of producing more than 227 kilograms polymer per hour (kg/hr) to about 90,900 kg/hr or higher, preferably greater than 455 kg/hr, more preferably greater than 4,540 kg/hr, even more preferably greater than 11,300 kg/hr, still more preferably greater than 15,900 kg/hr, still even more preferably greater than 22,700 kg/hr, and preferably greater than 29,000 kg/hr to greater than 45,500 kg/hr, and most preferably over 45,500 kg/hr.

The polymerization in a stirred bed can take place in one or two horizontal stirred vessels according to the polymerization mode. The reactors can be subdivided into individually gas-composition-controllable and/or polymerization-temperature-controllable polymerization compartments. With continuous catalyst injection, essentially at one end of the reactor, and powder removal at the other end, the residence time distribution approaches that of plug flow reactor. Preferably the fluorocarbon, if present, is introduced into the first stirred vessel.

Other gas phase processes contemplated by the processes discussed and described herein can include those described in U.S. Pat. Nos. 5,627,242; 5,665,818; and 5,677,375; and European Patent Application Publications EP-A-0 794 200; EP-A-0 802 202; and EP-B-634 421.

In another preferred embodiment the catalyst system is in liquid, suspension, dispersion, and/or slurry form and can be introduced into the gas phase reactor into a resin particle lean zone. Introducing a liquid, suspension, dispersion, and/or slurry catalyst system into a fluidized bed polymerization into a particle lean zone can be as discussed and described in U.S. Pat. No. 5,693,727.

In some embodiments, the gas phase polymerization can operate in the absence of fluorocarbon. In some embodiments, the gas phase polymerization can be conducted in the presence of a fluorocarbon. Generally speaking the fluorocarbons can be used as polymerization media and/or as condensing agents.

Slurry Phase Polymerization

A slurry polymerization process generally operates at a pressure range between about 103 kPa to about 5,068 kPa or even greater and a temperature from about 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane medium having from about 3 to about 7 carbon atoms, preferably a branched alkane. The medium employed can be liquid under the conditions of polymerization and relatively inert. When a propane medium is used the process can be operated above the reaction diluent critical temperature and pressure. Preferably, a hexane or an isobutane medium is employed.

In one embodiment, a preferred polymerization technique, referred to as a particle form polymerization or a slurry process, can include maintaining the temperature below the temperature at which the polymer goes into solution. Such technique is well known in the art, and can be as discussed and described in U.S. Pat. No. 3,248,179. The preferred temperature in the particle form process can be from about 20° C. to about 110° C. Two preferred polymerization processes for the slurry process can include those employing a loop reactor and those utilizing a plurality of stirred reactors in series, parallel, or combinations thereof. Non-limiting examples of slurry processes include continuous loop or stirred tank processes. Also, other examples of slurry processes can be as discussed and described in U.S. Pat. No. 4,613,484.

In another embodiment, the slurry process can be carried out continuously in a loop reactor. The catalyst, as a slurry in mineral oil and/or paraffinic hydrocarbon or as a dry, free flowing powder, can be injected regularly to the reactor loop, which can be filled with a circulating slurry of growing polymer particles in a diluent containing monomer and comonomer. Hydrogen, optionally, can be added as a molecular weight control. The reactor can be operated at a pressure of about 3,620 kPa to about 4,309 kPa and at a temperature from about 60° C. to about 115° C. depending on the desired polymer melting characteristics. Reaction heat can be removed through the loop wall since much of the reactor is in the form of a double-jacketed pipe. The slurry is allowed to exit the reactor at regular intervals or continuously to a heated low pressure flash vessel, rotary dryer, and a nitrogen purge column in sequence for removal of the diluent and at least a portion of any unreacted monomer and/or comonomers. The resulting hydrocarbon free powder can be compounded for use in various applications.

The reactor used in the slurry process can produce greater than 907 kg/hr, more preferably greater than 2,268 kg/hr, and most preferably greater than 4,540 kg/hr polymer. In another embodiment the slurry reactor can produce greater than 6,804 kg/hr, preferably greater than 11,340 kg/hr to about 45,500 kg/hr. The reactor used in the slurry process can be at a pressure from about 2,758 kPa to about 5,516 kPa, preferably about 3,103 kPa to about 4,827 kPa, more preferably from about 3,448 kPa to about 4,482 kPa, most preferably from about 3,620 kPa to about 4,309 kPa.

The concentration of the predominant monomer in the reactor liquid medium in the slurry process can be from about 1 wt % to about 30 wt %, preferably from about 2 wt % to about 15 wt %, more preferably from about 2.5 wt % to about 10 wt %, most preferably from about 3 wt % to about 20 wt %.

In one or more embodiments, the slurry and/or gas phase polymerization can be operated in the absence of or essentially free of any scavengers, such as triethylaluminum, trimethylaluminum, tri-isobutylaluminum and tri-n-hexylaluminum and diethyl aluminum chloride, dibutyl zinc and the like. Operation of the slurry and/or gas phase reactors in the absence or essentially free of any scavengers can be as discussed and described in WO Publication No. WO 96/08520 and U.S. Pat. No. 5,712,352. In another embodiment the polymerization processes can be run with scavengers. Typical scavengers include trimethyl aluminum, tri-ethyl aluminum, tri-isobutyl aluminum, tri-n-octyl aluminum, and an excess of alumoxane and/or modified alumoxane.

In some embodiments, the slurry phase polymerization can operate in the absence of a fluorocarbon. In some embodiments, the slurry phase polymerization can be conducted in the presence of a fluorocarbon. Generally speaking the fluorocarbons can be used as polymerization media.

Solution Phase Polymerization

As used herein, the phrase "solution phase polymerization" refers to a polymerization system where the polymer produced is soluble in the polymerization medium. Generally this involves polymerization in a continuous reactor in which the polymer formed and the starting monomer and catalyst materials supplied, are agitated to reduce or avoid concentration gradients and in which the monomer acts as a diluent or solvent or in which a hydrocarbon is used as a diluent or solvent. Suitable processes typically operate at temperatures from about 0° C. to about 250° C., preferably from about 10° C. to about 150° C., more preferably from about 40° C. to about 140° C., more preferably from about 50° C. to about 120° C. and at pressures of about 0.1 MPa or more, preferably 2 MPa or more. The upper pressure limit is not critically constrained but typically can be about 200 MPa or less, preferably, 120 MPa or less. Temperature control in the reactor can generally be obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds can also be used. The purity, type, and amount of solvent can be optimized for the maximum catalyst productivity for a particular type of polymerization. The solvent can be also introduced as a catalyst carrier. The solvent can be introduced as a gas phase or as a liquid phase depending on the pressure and temperature. Advantageously, the solvent can be kept in the liquid phase and introduced as a liquid. Solvent can be introduced in the feed to the polymerization reactors.

In a preferred embodiment, the polymerization process can be described as a continuous, non-batch process that, in its steady state operation, is exemplified by removal of amounts of polymer made per unit time, being substantially equal to the amount of polymer withdrawn from the reaction vessel per unit time. By "substantially equal" we intend that these amounts, polymer made per unit time, and polymer withdrawn per unit time, are in ratios of one to other, of from 0.9:1; or 0.95:1; or 0.97:1; or 1:1. In such a reactor, there will be a substantially homogeneous monomer distribution.

Preferably in a continuous process, the mean residence time of the catalyst and polymer in the reactor generally can be from about 5 minutes to about 8 hours, and preferably from about 10 minutes to about 6 hours, more preferably from 10 minutes to 1 hour. In some embodiments, comonomer (such as ethylene) can be added to the reaction vessel in an amount to maintain a differential pressure in excess of the combined vapor pressure of the main monomer (such as a propylene) and any optional diene monomers present.

In another embodiment, the polymerization process can be carried out at a pressure of ethylene of from about 68 kPa to about 6,800 kPa, most preferably from about 272 to about 5,440 kPa). The polymerization is generally conducted at a temperature of from about 25° C. to about 250° C., preferably from about 75° C. to about 200° C., and most preferably from about 95° C. to about 200° C.

The addition of a small amount of hydrocarbon to a typical solution phase process can cause the polymer solution viscosity to drop and or the amount of polymer solute to increase. Addition of a larger amount of solvent in a traditional solution process can cause the separation of the polymer into a separate phase (which can be solid or liquid, depending on the reaction conditions, such as temperature or pressure).

The processes discussed and described herein can be carried out in continuous stirred tank reactors, batch reactors, or plug flow reactors. One reactor can be used even if sequential polymerizations are being performed, preferably as long as there is separation in time or space of the two reactions. Likewise two or more reactors operating in series or parallel can also be used. These reactors can have or not have internal cooling and the monomer feed may or may not be refrigerated. See the general disclosure of U.S. Pat. No. 5,001,205 for general process conditions. See also, WO Publication Nos. WO 96/33227 and WO 97/22639.

As previously noted, the processes described above can optionally use more than one reactor. The use of a second reactor is especially useful in those embodiments in which an additional catalyst, especially a Ziegler-Natta or chrome catalyst, or by proper selection of process conditions, including catalyst selection, polymers with tailored properties can be produced. The cocatalysts and optional scavenger components in the process can be independently mixed with the catalyst component before introduction into the reactor, or they can each independently be fed into the reactor using separate streams, resulting in "in reactor" activation. Each of the above processes can be employed in single reactor, parallel or series reactor configurations. In series operation, the second reactor temperature is preferably higher than the first reactor temperature. In parallel reactor operation, the temperatures of the two reactors can be independent. The pressure can vary from about 0.1 kPa to about 250 MPa, preferably from about 0.01 MPa to about 160 MPa, most preferably from 0.1 MPa to about 50 MPa. The liquid processes can include contacting olefin monomers with any one or more of the catalyst systems discussed and described herein in a suitable diluent or solvent and allowing the monomers to react for a sufficient time to produce the desired polymers. In multiple reactor processes the solvent can be introduced into one or all of the reactors. In particular, a first solvent can be introduced into the first reactor, and a second solvent, which can be the same or different from the first solvent, can be introduced into the second reactor. Likewise the solvent can be introduced in the first reactor alone or the second reactor alone. In addition to the above, in multiple reactor configurations where there is a third, fourth or fifth reactor, the solvent can be introduced into all of the third, fourth and fifth reactors, none of the third, fourth and fifth reactors, just the third reactor, just the fourth reactor, just the fifth reactor, just the third and fourth reactors, just the third and fifth reactors, or just the fourth and fifth reactors. Likewise, any solvent introduced to any of the third, fourth, and/or fifth reactors can be the same or different as the first and/or second solvents.

In another embodiment, a sequential polymerization process is used and the first polymerization is a slurry process to produce homopolymer followed by another slurry reactor for impact copolymer (ICP) production. Impact copolymers can be produced by first making homopolypropylene in a slurry reactor, and transferring the homopolypropylene to another slurry reactor where copolymers are produced with the presence of homopolypropylene. Fluorocarbon can be introduced into the first reactor, the second reactor or both. The catalyst compounds described herein may be used in the first step for ICP production to produce thermoplastic polymer such as homopolypropylene or may be used in the second step to produce thermoplastic polymer such as a copolymer of propylene and ethylene.

In another embodiment, the two (or more) polymerizations can occur in the same reactor but in different reaction zones. For example, another preferred embodiment is process to prepare impact copolymers comprising producing a semi-crystalline polymer in a first reaction zone and then transferring the semi-crystalline polymer to a second reaction zone where a low crystallinity polymer can be produced in the presence of the semi-crystalline polymer.

In any of the embodiments above the first reactor and second reactor can be reaction zones in the same reactor. Reactors where multiple reaction zones are possible include Spherizone™ type reactors and those described in U.S. Pat. No. 6,413,477.

In a particular embodiment, the impact copolymer can be produced in situ within three reactors, where a first polypropylene is produced in a first reactor, a second polypropylene is produced in a second reactor, and the ethylene copolymer or elastomeric polymer is produced in a third reactor, with each reactor associated in series. In another particular embodiment, the impact copolymer can be produced in situ within three reactors, where the first polypropylene is produced in the first reactor with a first catalyst composition and the second polypropylene is produced in the second reactor with a second catalyst composition, where the first and second catalyst compositions differ from one another, and the elastomeric polymer is produced in the third reactor, each reactor associated in series.

In a particular embodiment, the first and second reactors can be slurry-loop reactors and the third reactor can be a gas phase reactor. The first and second reactors can produce the polypropylenes, homopolymers in a particular embodiment, and the gas phase reactor can produce the ethylene copolymer or elastomeric polymer, thus creating an in situ blend of the ethylene copolymer in the polypropylene matrix. The impact copolymer can include from a low of about 30 wt %, about 35 wt %, or about 40 wt % to a high of about 60 wt %, about 65 wt %, or about 70 wt % of the first polypropylene, based on the total weight of the impact copolymer. The impact copolymer can also include from a low of about 10 wt %, about 15 wt %, or about 20 wt % to a high of about 30 wt %, about 35 wt %, or about 40 wt % of the second polypropylene, based on the total weight of the impact copolymer. The impact copolymer can also include from a low of about 15 wt %, about 20 wt %, or about 22 wt % to a high of about 26 wt %, about 30 wt %, or about 35 wt % of the ethylene copolymer, based on the total weight of the impact copolymer. These amounts can be achieved, in the case where one or more reactors is used to produce the propylene impact copolymer, by any suitable means known to those skilled in the art including control of the residence time in each stage and/or reactor, the amount and/or particular catalyst composition(s), variation in the reactants in each stage and/or reactor (i.e., propylene, comonomer, hydrogen, etc. concentrations), combinations of these, and/or any other means.

In embodiments where one or more reactors are used to produce the impact copolymer(s), one or more chain terminating agent(s) (e.g., hydrogen) can be used to control the MFR (molecular weight) of the polypropylene(s). The chain terminating agents can be used as a means of adjusting the MFR of components of the impact copolymer either alone or in conjunction with other means. In a particular embodiment, the process of producing the impact copolymer can include contacting a catalyst with propylene, a first amount of a chain terminating agent, and optionally one or more comonomers, e.g., ethylene and/or $C_4$ to $C_{12}$ α-olefins, in a first reactor to form a first polypropylene comprising no more than 5 wt % of ethylene and/or α-olefin derived units, based on the weight of the first polypropylene. The catalyst and the first polypropylene can be contacted with propylene, a second amount of a chain terminating agent, and optionally one or more comonomers, e.g., ethylene and/or $C_4$ to $C_{12}$ α-olefins in a second reactor to form a second polypropylene comprising no more than 5 wt % of ethylene and/or α-olefin derived units, based on the weight of the second polypropylene. The second amount of chain terminating agent can be greater than the first amount of chain terminating agent. Finally, the catalyst composition, the first polypropylene, and the second polypropylene can be contacted with propylene and ethylene in a third reactor to form an ethylene-propylene copolymer that includes from about 35 wt % or about 40 wt % or about 45 wt % to about 60 wt % or about 65 wt %, or about 70 wt % ethylene-derived units, based on the weight of the impact copolymer.

The first amount of the chain terminating agent can be added to the one or more reactors and/or one or more stages within the reactor(s) such that the first polypropylene has an $MFR_1$ from a low of about 8 dg/min, about 15 dg/min, or about 18 dg/min to a high of about 33 dg/min, about 35 dg/min, or about 40 dg/min. The second amount of chain terminating agent can be added (in certain embodiments) such that the second polypropylene has an $MFR_2$ from a low of about 50 dg/min, about 65 dg/min, or about 70 dg/min to a high of about 100 dg/min, about 120 dg/min, or about 190 dg/min. Described another way, the second amount of chain terminating agent (in certain embodiments) can be greater than the first amount of chain terminating agent such that the $MFR_1$ of the first polypropylene is at least 30% less, at least 35% less, at least 40% less, at least 45% less, or at least 50% less than the MFR2 of the second polypropylene. Stated in yet another way, the chain terminating agent(s) can be added to the reactor(s) such that MFR2/MFR1 is from a low of about 2, about 2.5, or about 3 to a high of about 4, about 4.5, about 5, or about 6 in certain embodiments, and greater than 1.5, greater than 2.0, greater than 2.5, or greater than 3 in other embodiments. The amount of chain terminating agent can be varied by any suitable means in the reactor(s), and in one embodiment the amount of the first chain terminating agent can be less than 2,000 mol ppm or less than 1,800 mol ppm as measured in the first propylene feed to the reactor, and the amount of the second chain terminating agent can be greater than 2,500 mol ppm or greater than 2,800 mol ppm as measured in the second propylene feed to the reactor.

In certain embodiments of the three reactor process, catalyst components, propylene, chain terminating agent, and any other optional monomers can be fed to a first loop reactor for a first homopolymerization or copolymerization process. The high heat removal capability of the loop reactor can cause or facilitate turbulent mixing of the slurry and the large surface-to-volume ratio of the reactor can enable high specific outputs. Operating conditions are typically in the range of about 60° C. to about 80° C., about 500 psi to about 700 psi, and an amount of chain terminating agent, hydrogen in a preferred embodiment, of less than about 2,000 mol ppm or less than about 1,800 mol ppm as measured in the propylene feed to the reactor, and within the range from about 1,000 mol ppm, about 1,100 mol ppm, or about 1,200 mol ppm to about 1,800 mol ppm, or about 2,000 mol ppm in another embodiment. The polymer produced from the first reactor (along with residual chain terminating agent and monomers) can be transferred to a second loop reactor where the operating conditions can be the same or different with respect to the first loop reactor. Additional monomer, chain terminating agent, and optional comonomer can be added also. In a particular embodiment, at least the amount of the second chain terminating agent will be different, where the amount of chain terminating agent, hydrogen in a preferred embodiment, is greater than 2,500 mol ppm or greater than 2,800 mol ppm as measured in the propylene feed to the second reactor, and within the range of about 2,500 mol ppm, about 3,000 mol ppm, or about 3,400 mol ppm to about 3,600 mol ppm, or about 4,000 mol ppm in another embodiment.

Upon exiting the second loop reactor, the polypropylene slurry can be depressurized and flashed at a pressure that allows for recycle of the vaporized monomer(s) by condensation using cooling water or other cooling means, and can be sufficient for gas phase polymerization. The polypropylene and catalyst composition mixture can be transferred to a gas phase reactor. The ethylene copolymer or elastomeric polymer can be produced within this gas phase reactor in certain embodiments. The ethylene copolymer, an ethylene-propylene copolymer in a preferred embodiment, can be produced in a particular embodiment by use of a fluidized bed gas phase reactor operating at a temperature from a low of about 50° C., about 60° C., or about 70° C. to a high of about 80° C., about 90° C., about 100° C., about 110° C., or about 120° C., and pressures from a low of about 100 psi, about 125 psi, or about 150 psi to a high of about 200 psi, about 250 psi, or about 300 psi. Polymer exiting the polymerization section can pass through a low pressure separator, in which the remaining monomer can be separated for recycle. A steam treatment vessel for deactivation of the residual catalyst can present in certain embodiments. A small fluid bed dryer or other drying means can also be present. An example of such a process can include the so called "Spheripol" reactor process.

The catalyst composition in the second or third reactors may be the compound described herein or can be any suitable catalyst composition known for polymerizing olefins to produce polyolefins and is desirably a composition that can control the isotacticity of the polymers that are produced. Non-limiting examples of suitable catalysts compositions include Ziegler-Natta catalysts, metallocene catalysts, chromium catalysts, metal-imide/amine coordination catalysts, and combinations of such catalysts each with its desirable co-catalyst and/or electron donor or other modifying agent known in the art. An example of certain desirable catalyst compositions can be as discussed and described in WO Publication No. WO99/20663, e.g., a Ziegler-Natta catalyst composition using any one of a combination of aluminum alkyl donor systems. The selection of other conditions for producing the individual impact copolymer components and the whole propylene impact copolymer is reviewed by, for example, G. DiDrusco and R. Rinaldi in "Polypropylene-Process Selection Criteria" in HYDROCARBON PROCESSING 113 (November 1984), and references cited therein.

In a preferred embodiment, a sequential polymerization process can be used and the first polymerization can be a slurry process to produce homopolymer followed by a gas-phase process for producing the impact copolymer. The slurry process can be a loop reactor or a CSTR type of reactor. In a loop reactor, the first reaction stage can include one or two tubular loop reactors where bulk polymerization of homopolymers can be carried out in liquid propylene. The catalyst, e.g., a prepolymerized catalyst, and liquid propylene, and hydrogen for controlling molecular weight can be fed into the reactor. The homopolymer in liquid propylene inside the loops can be continuously discharged to a separation unit. Unreacted propylene can be recycled to the reaction medium while the polymer can be transferred to one or two gas phase reactors where ethylene, propylene, and hydrogen can be added to produce the impact copolymers. The granules can be discharged to the monomer flashing and recovery section and sent to a monomer stripping system. After the drying unit, the granular resin can be conveyed to an extrusion system for stabilization, and pelletization.

Supercritical or Supersolution Polymerization

Definitions

A dense fluid is a liquid or supercritical fluid having a density of at least 300 kg/m$^3$.

The solid-fluid phase transition temperature is defined as the temperature below which a solid polymer phase separates from the homogeneous polymer-containing fluid medium at a given pressure. The solid-fluid phase transition temperature can be determined by temperature reduction at constant pressure starting from temperatures at which the polymer is fully dissolved in the fluid medium. The phase transition is observed as the system becoming turbid, when measured using the method described below for determining cloud point.

The solid-fluid phase transition pressure is defined as the pressure below which a solid polymer phase separates from the polymer-containing fluid medium at a given temperature. The solid-fluid phase transition pressure is determined by pressure reduction at constant temperature starting from pressures at which the polymer is fully dissolved in the fluid medium. The phase transition is observed as the system becoming turbid, when measured using the method described below for determining cloud point.

The fluid-fluid phase transition pressure is defined as the pressure below which two fluid phases—a polymer-rich phase and a polymer-lean phase—form at a given temperature. The fluid-fluid phase transition pressure can be determined by pressure reduction at constant temperature starting from pressures at which the polymer is fully dissolved in the fluid medium. The phase transition is observed as the system becoming turbid, when measured using the method described below for determining cloud point.

The fluid-fluid phase transition temperature is defined as the temperature below which two fluid phases—a polymer-rich phase and a polymer-lean phase—form at a given pressure. The fluid-fluid phase transition temperature can be determined by temperature reduction at constant pressure starting from temperatures at which the polymer is fully dissolved in the fluid medium. The phase transition is observed as the system becoming turbid, when measured using the method described below for determining cloud point.

The cloud point is the pressure below which, at a given temperature, the polymerization system becomes turbid as described in J. Vladimir Oliveira, C. Dariva and J. C. Pinto, Ind. Eng, Chem. Res. 29, 2000, p. 4627. For purposes of this invention and the claims thereto, the cloud point is measured by shining a helium laser through the selected polymerization system in a cloud point cell onto a photocell and recording the pressure at the onset of rapid increase in light scattering for a given temperature. Cloud point pressure is the point at which at a given temperature, the polymerization system becomes turbid. Cloud point temperature is the point at which at a given pressure, the polymerization system becomes turbid. It should be noted that although both the cloud point pressure and cloud point temperature are well-defined physical properties, in the area of polymer engineering, "cloud point" typically refers to the cloud point pressure.

To be in the supercritical state, a substance must have a temperature above its critical temperature (Tc) and a pressure above its critical pressure (Pc). The critical temperature and pressure vary with composition of polymerization medium. If not measured, critical temperatures (Tc) and critical pressures (Pc) are those found in the Handbook of Chemistry and Physics, David R. Lide, Editor-in-Chief, 82nd edition 2001-2002, CRC Press, LLC. New York, 2001. In particular, the Tc and Pc of propylene are 364.9 K and 4.6 MPa. In the event a Tc and/or Pc cannot be measured for a given system, then the Tc and/or Pc will be deemed to be the Tc and/or Pc of the mole fraction weighted averages of the corresponding Tc's and Pc's of the system components.

The term "continuous" means a system that operates without interruption or cessation. For example a continuous process to produce a polymer would be one where the reactants are continually introduced into one or more reactors and polymer product is continually withdrawn.

A solution polymerization means a polymerization process in which the polymer is dissolved in a liquid polymerization system, such as an inert solvent or monomer(s) or their blends. A solution polymerization is typically a homogeneous liquid polymerization system.

A supercritical polymerization means a polymerization process in which the polymerization system is in a dense (i.e. its density is 300 kg/m$^3$ or higher), supercritical state.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger.

A bulk polymerization system typically contains 30 volume % or less of solvents, preferably less than 25 wt % of inert solvent or diluent.

A homogeneous polymerization or a homogeneous polymerization system is a polymerization system where the polymer product is dissolved in the polymerization medium. Such systems are not turbid as described in J. Vladimir Oliveira, C. Dariva and J. C. Pinto, Ind. Eng, Chem. Res. 29, 2000, p. 4627. For purposes of this invention and the claims thereto, turbidity is measured by shining a helium laser through the selected polymerization system in a cloud point cell onto a photocell and determining the point of the onset of rapid increase in light scattering for a given polymerization system. Uniform dissolution in the polymerization medium is indicated when there is little or no light scattering (i.e. less than 5%).

A super solution polymerization or supersolution polymerization system is one where the polymerization occurs at a temperature of 65° C. to 150° C. and a pressure of between 250 to 5,000 psi (1.72 to 34.5 MPa), having: 1) 0 to 20 wt % of one or more comonomers (based upon the weight of all monomers and comonomers present in the feed) selected from the group consisting of ethylene and $C_4$ to $C_{12}$ olefins, 2) from 20 to 65 wt % diluent or solvent, based upon the total weight of feeds to the polymerization reactor, 3) 0 to 5 wt % scavenger, based upon the total weight of feeds to the polymerization reactor, 4) the olefin monomers and any comonomers are present in the polymerization system at 15 wt % or more, 5) the polymerization temperature is above the solid-fluid phase transition temperature of the polymerization system and above a pressure greater than 1 MPa below the cloud point pressure of the polymerization system, provided however that the polymerization occurs: (1) at a temperature below the critical temperature of the polymerization system, or (2) at a pressure below the critical pressure of the polymerization system.

Supercritical or Supersolution Polymerization Process

The present polymerization process may be conducted under homogeneous (such as solution, supersolution, or supercritical) conditions preferably including a temperature of about 60° C. to about 200° C., preferably for 65° C. to 195° C., preferably for 90° C. to 190° C., preferably from greater than 100° C. to about 180° C., such as 105° C. to 170° C., preferably from about 110° C. to about 160° C. and a pressure in excess of 1.7 MPa, especially under supersolution conditions including a pressure of between 1.7 MPa and 30 MPa, or especially under supercritical conditions including a pressure of between 15 MPa and 1500 MPa, especially when the monomer composition comprises propylene or a mixture of propylene with at least one $C_4$ to $C_{20}$ α-olefin. In a preferred embodiment the monomer is propylene and the propylene is present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more. In an alternate embodiment, the monomer and any comonomer present are present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more.

In a particular embodiment of the invention, the polymerization process is conducted under supersolution conditions including temperatures from about 65° C. to about 150° C., preferably from about 75° C. to about 140° C., preferably from about 90° C. to about 140° C., more preferably from about 100° C. to about 140° C., and pressures of between 1.72 MPa and 35 MPa, preferably between 5 and 30 MPa.

In another particular embodiment of the invention, the polymerization process is conducted under supercritical conditions (preferably homogeneous supercritical conditions, e.g. above the supercritical point and above the cloud point) including temperatures from about 90° C. to about 200° C., and pressures of between 15 MPa and 1500 MPa, preferably between 20 MPa and 140 MPa.

A particular embodiment of this invention relates to a process to polymerize propylene comprising contacting, at a temperature of 60° C. or more and a pressure of between 15 MPa (150 Bar, or about 2175 psi) to 1500 MPa (15,000 Bar, or about 217,557 psi), one or more olefin monomers having three or more carbon atoms, with: 1) the catalyst system, 2) optionally one or more comonomers, 3) optionally diluent or solvent, and 4) optionally scavenger, wherein: a) the olefin monomers and any comonomers are present in the polymerization system at 40 wt % or more, b) the propylene is present at 80 wt % or more based upon the weight of all monomers and comonomers present in the feed, c) the polymerization occurs at a temperature above the solid-fluid phase transition temperature of the polymerization system and a pressure no lower than 2 MPa below the cloud point pressure of the polymerization system.

Another particular embodiment of this invention relates to a process to polymerize olefins comprising contacting propylene, at a temperature of 65° C. to 150° C. and a pressure of between 250 to 5,000 psi (1.72 to 34.5 MPa), with: 1) the catalyst system, 2) 0 to 20 wt % of one or more comonomers (based upon the weight of all monomers and comonomers present in the feed) selected from the group consisting of ethylene and $C_4$ to $C_{12}$ olefins, 3) from 20 to 65 wt % diluent or solvent, based upon the total weight of feeds to the polymerization reactor, and 4) 0 to 5 wt % scavenger, based upon the total weight of feeds to the polymerization reactor, wherein: a) the olefin monomers and any comonomers are present in the polymerization system at 15 wt % or more, b) the propylene is present at 80 wt % or more based upon the weight of all monomers and comonomers present in the feed, c) the polymerization occurs at a temperature above the solid-fluid phase transition temperature of the polymerization system and above a pressure greater than 1 MPa below the cloud point pressure of the polymerization system, provided however that the polymerization occurs: (1) at a temperature below the critical temperature of the polymerization system, or (2) at a pressure below the critical pressure of the polymerization system.

In another embodiment, the polymerization occurs at a temperature above the solid-fluid phase transition temperature of the polymerization system and a pressure no lower than 10 MPa below the cloud point pressure (CPP) of the polymerization system (preferably no lower than 8 MPa below the CPP, preferably no lower than 6 MPa below the CPP, preferably no lower than 4 MPa below the CPP, preferably no lower than 2 MPa below the CPP). Preferably, the polymerization occurs at a temperature and pressure above the solid-fluid phase transition temperature and pressure of the polymerization system and, preferably above the fluid-fluid phase transition temperature and pressure of the polymerization system.

In an alternate embodiment, the polymerization occurs at a temperature above the solid-fluid phase transition temperature of the polymerization system and a pressure greater than 1 MPa below the cloud point pressure (CPP) of the polymerization system (preferably greater than 0.5 MPa below the CPP, preferably greater than the CPP), and the polymerization occurs: (1) at a temperature below the critical temperature of the polymerization system, or (2) at a pressure below the critical pressure of the polymerization system, preferably the polymerization occurs at a pressure and temperature below the critical point of the polymerization system, most preferably the polymerization occurs: (1) at a temperature below the critical temperature of the polymerization system, and (2) at a pressure below the critical pressure of the polymerization system.

Alternately, the polymerization occurs at a temperature and pressure above the solid-fluid phase transition temperature and pressure of the polymerization system. Alternately, the polymerization occurs at a temperature and pressure above the fluid-fluid phase transition temperature and pressure of the polymerization system. Alternately, the polymerization occurs at a temperature and pressure below the fluid-fluid phase transition temperature and pressure of the polymerization system.

In another embodiment, the polymerization system is preferably a homogeneous, single phase polymerization system, preferably a homogeneous dense fluid polymerization system.

In another embodiment, the reaction temperature is preferably below the critical temperature of the polymerization system. Preferably, the temperature is above the solid-fluid phase transition temperature of the polymer-containing fluid reaction medium at the reactor pressure or at least 5° C. above the solid-fluid phase transition temperature of the polymer-containing fluid reaction medium at the reactor pressure, or at least 10° C. above the solid-fluid phase transformation point of the polymer-containing fluid reaction medium at the reactor pressure. In another embodiment, the temperature is above the cloud point of the single-phase fluid reaction medium at the reactor pressure, or 2° C. or more above the cloud point of the fluid reaction medium at the reactor pressure. In yet another embodiment, the temperature is between 60° C. and 150° C., between 60° C. and 140° C., between 70° C. and 130° C., or between 80° C. and 130° C. In one embodiment, the temperature is above 60° C., 65° C., 70° C., 75° C., 80° C., 85° C., 90° C., 95° C., 100° C., 105° C., or 110° C. In another embodiment, the temperature is below 150° C., 140° C., 130° C., or 120° C. In another embodiment, the cloud point temperature is below the supercritical temperature of the polymerization system or between 70° C. and 150° C.

In another embodiment, the polymerization occurs at a temperature and pressure above the solid-fluid phase transition temperature of the polymerization system, preferably the polymerization occurs at a temperature at least 5° C. higher (preferably at least 10° C. higher, preferably at least 20° C. higher) than the solid-fluid phase transition temperature and at a pressure at least 2 MPa higher (preferably at least 5 MPa higher, preferably at least 10 MPa higher) than the cloud point pressure of the polymerization system. In a preferred embodiment, the polymerization occurs at a pressure above the fluid-fluid phase transition pressure of the polymerization system (preferably at least 2 MPa higher, preferably at least 5 MPa higher, preferably at least 10 MPa higher than the fluid-fluid phase transition pressure). Alternately, the polymerization occurs at a temperature at least 5° C. higher (preferably at least 10° C. higher, preferably at least 20° C. higher) than the solid-fluid phase transition temperature and at a pressure higher than, (preferably at least 2 MPa higher, preferably at least 5 MPa higher, preferably at least 10 MPa higher) than the fluid-fluid phase transition pressure of the polymerization system.

In another embodiment, the polymerization occurs at a temperature above the solid-fluid phase transition temperature of the polymer-containing fluid reaction medium at the reactor pressure, preferably at least 5° C. above the solid-fluid phase transition temperature of the polymer-containing fluid reaction medium at the reactor pressure, or preferably at least 10° C. above the solid-fluid phase transformation point of the polymer-containing fluid reaction medium at the reactor pressure.

In another useful embodiment, the polymerization occurs at a temperature above the cloud point of the single-phase fluid reaction medium at the reactor pressure, more preferably 2° C. or more (preferably 5° C. or more, preferably 10° C. or more, preferably 30° C. or more) above the cloud point of the fluid reaction medium at the reactor pressure. Alternately, in another useful embodiment, the polymerization occurs at a temperature above the cloud point of the polymerization system at the reactor pressure, more preferably 2° C. or more (preferably 5° C. or more, preferably 10° C. or more, preferably 30° C. or more) above the cloud point of the polymerization system.

In another embodiment, the polymerization process temperature is above the solid-fluid phase transition temperature of the polymer-containing fluid polymerization system at the reactor pressure, or at least 2° C. above the solid-fluid phase transition temperature of the polymer-containing fluid polymerization system at the reactor pressure, or at least 5° C. above the solid-fluid phase transition temperature of the polymer-containing fluid polymerization at the reactor pressure, or at least 10° C. above the solid-fluid phase transformation point of the polymer-containing fluid polymerization system at the reactor pressure. In another embodiment, the polymerization process temperature should be above the cloud point of the single-phase fluid polymerization system at the reactor pressure, or 2° C. or more above the cloud point of the fluid polymerization system at the reactor pressure. In still another embodiment, the polymerization process temperature is between 50° C. and 350° C., or between 60° C. and 250° C., or between 70° C. and 250° C., or between 80° C. and 250° C. Exemplary lower polymerization temperature limits are 50° C., or 60° C., or 70° C., or 80° C., or 90° C., or 95° C., or 100° C., or 110° C., or 120° C. Exemplary upper polymerization temperature limits are 350° C., or 250° C., or 240° C., or 230° C., or 220° C., or 210° C., or 200° C.

Polyolefin Products

This invention also relates to compositions of matter produced by the methods described herein.

In a preferred embodiment, the process described herein produces propylene homopolymers or propylene copolymers, such as propylene-ethylene and/or propylene-alphaolefin (preferably $C_3$ to $C_{20}$) copolymers (such as propylene-hexene copolymers or propylene-octene copolymers) having: a Mw/Mn of greater than 1 to 4 (preferably greater than 1 to 3).

Likewise, the process of this invention produces olefin polymers, preferably polyethylene and polypropylene homopolymers and copolymers. In a preferred embodiment, the polymers produced herein are homopolymers of ethylene or propylene, are copolymers of ethylene preferably having from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene), or are copolymers of propylene preferably having from 0 to 25 mole % (alternately from 0.5 to 20 mole %, alternately from 1 to 15 mole %, preferably from 3 to 10 mole %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

In a preferred embodiment, the monomer is ethylene and the comonomer is hexene, preferably from 1 to 15 mole % hexene, alternately 1 to 10 mole %.

Typically, the polymers produced herein have an Mw (as measured by GPC-DRI) from 5,000 to 1,000,000 g/mol, alternately from 20,000 to 1,000,000 g/mol, alternately 100,000 to 800,000 g/mol, alternately 200,000 to 600,000 g/mol, alternately from 300,000 to 550,000 g/mol, alternately from 330,000 g/mol to 500,000 g/mol.

Typically, the polymers produced herein have an Mw/Mn (as measured by GPC-DRI) of greater than 1 to 20, preferably 1.1 to 15, preferably 1.2 to 10, preferably 1.3 to 5, preferably 1.4 to 4.

Typically, the polymers produced herein have an Mw (as measured by GPC-DRI) of 5,000 to 1,000,000 g/mol (preferably 25,000 to 750,000 g/mol, preferably 50,000 to 500,000 g/mol), and/or an Mw/Mn of greater than 1 to 40 (alternately 1.1 to 20, alternately 1.2 to 10, alternately 1.3 to 5, 1.4 to 4, alternately 1.4 to 3).

In a preferred embodiment the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

The polymer produced herein can have a melting point (Tm, DSC peak second melt) of at least 145° C., or at least 150° C., or at least 152° C., or at least 153° C., or at least 154° C. For example, the polymer can have a melting point from at least 145° C. to about 175° C., about 150° C. to about 165° C., about 152° C. to about 160° C.

The polymer produced herein can have a 1% secant flexural modulus from a low of about 1100 MPa, about 1200 MPa, about 1250 MPa, about 1300 MPa, about 1400 MPa, or about 1,500 MPa to a high of about 1,800 MPa, about 2,100 MPa, about 2,600 MPa, or about 3,000 MPa, as measured according to ASTM D 790 (A, 1.0 mm/min). For example, the polymer can have a flexural modulus from about 1100 MPa to about 2,200 MPa, about 1200 MPa to about 2,000 MPa, about 1400 MPa to about 2,000 MPa, or about 1500 MPa or more, as measured according to ASTM D 790 (A, 1.0 mm/min).

The polymer produced herein can have a melt flow rate (MFR) from a low of about 0.1 dg/min, about 0.2 dg/min, about 0.5 dg/min, about 1 dg/min, about 15 dg/min, about 30 dg/min, or about 45 dg/min to a high of about 75 dg/min, about 100 dg/min, about 200 dg/min, or about 300 dg/min. For example, the impact copolymer can have an MFR of about 0.5 dg/min to about 300 dg/min, about 1 dg/min to about 300 dg/min, about 5 dg/min to about 150 dg/min, or about 10 dg/min to about 100 dg/min, or about 20 dg/min to about 60 dg/min.

Impact Copolymer

The polymers produced herein can be used in impact copolymers. The impact copolymer (ICP) can include the polypropylene polymer produced herein and another polymer such as an ethylene copolymer. The morphology is typically such that the matrix phase is primarily the polypropylene polymer and the dispersed phase can be primarily the ethylene copolymer phase.

The impact copolymer can have a total propylene content of at least 75 wt %, at least 80 wt %, at least 85 wt %, at least 90 wt %, or at least 95 wt %, based on the weight of the impact copolymer.

The impact copolymer can have a total comonomer content from about 1 wt % to about 35 wt %, about 2 wt % to about 30 wt %, about 3 wt % to about 25 wt %, or about 5 wt % to about 20 wt %, based on the total weight of the impact copolymer, with the balance being propylene.

Preferred impact copolymers comprise isotactic polypropylene and ethylene copolymer and typically have an ethylene copolymer (preferably ethylene propylene copolymer) content from a low of about 5 wt %, about 8 wt %, about 10 wt %, or about 15 wt % to a high of about 25 wt %, about 30 wt %, about 38 wt %, or about 42 wt %. For example, the impact polymer can have an ethylene copolymer content of about 5 wt % to about 40 wt %, about 6 wt % to about 35 wt %, about 7 wt % to about 30 wt %, or about 8 wt % to about 30 wt %.

In preferred impact copolymers comprising isotactic polypropylene and ethylene copolymer, the impact copolymer can have a propylene content of the ethylene copolymer component from a low of about 25 wt %, about 37 wt %, or about 46 wt % to a high of about 73 wt %, about 77 wt %, or about 80 wt %, based on the based on a weight of the ethylene copolymer. For example, the impact copolymer can have a propylene content of the ethylene copolymer component from about 25 wt % to about 80 wt %, about 10 wt % to about 75 wt %, about 35 wt % to about 70 wt %, or at least 40 wt % to about 80 wt %, based on the weight of the ethylene copolymer.

In preferred impact copolymers comprising isotactic polypropylene and ethylene copolymer, the impact copolymer can have ratio of the intrinsic viscosity (IV, ASTM D 1601 −135° C. in decalin) of the ethylene copolymer component to the intrinsic viscosity of the polypropylene component from a low of about 0.5, about 1.5, about 3, or about 4 to a high of about 6, about 9, about 12, or about 15. For example, the impact copolymer component can have a ratio of the intrinsic viscosity of about 0.5 to about 15, about 0.75 to about 12, or about 1 to about 7.

The impact copolymer can have a propylene meso diads content in the polypropylene component 90% or more, 92% or more, about 94% or more, or about 96% or more. Polypropylene microstructure is determined according to the $^{13}C$ NMR procedure described in US 2008/0045638 at paragraph [0613].

The impact copolymer can have a weight average molecular weight (Mw) from a low of about 20 kg/mol, about 50 kg/mol, about 75 kg/mol, about 150 kg/mol, or about 300 kg/mol to a high of about 600 kg/mol, about 900 kg/mol, about 1,300 kg/mol, or about 2,000 kg/mol. For example, the ethylene copolymer can have a Mw of about 50 kg/mol to about 3,000 kg/mol, about 100 kg/mol to about 2,000 kg/mol, or about 200 kg/mol to about 1,000 kg/mol.

The impact copolymer can have a melt flow rate (MFR) from about 1 dg/min to about 300 dg/min, about 5 dg/min to about 150 dg/min, or about 10 dg/min to about 100 dg/min, or about 20 dg/min to about 60 dg/min.

The impact copolymer can have a melting point (Tm, peak second melt) from at least 100° C. to about 175° C., about 105° C. to about 170° C., about 110° C. to about 165° C., or about 115° C. to about 155° C.

The impact copolymer can have a heat of fusion ($H_f$, DSC second heat) of 60 J/g or more, 70 J/g or more, 80 J/g or more, 90 J/g or more, about 95 J/g or more, or about 100 J/g or more.

The impact copolymer can have a 1% secant flexural modulus from about 300 MPa to about 3,000 MPa, about 500 MPa to about 2,500 MPa, about 700 MPa to about 2,000 MPa, or about 900 MPa to about 1,500 MPa, as measured according to ASTM D 790 (A, 1.3 mm/min).

The impact copolymer can have a notched Izod impact strength at 23° C. of about 2.5 KJ/m$^2$ or more, about 5 KJ/m$^2$ or more, about 7.5 KJ/m$^2$ or more, about 10 KJ/m$^2$ or more, about 15 KJ/m$^2$ or more, about 20 KJ/m$^2$ or more, about 25 KJ/m$^2$ or more, or about 50 KJ/m$^2$ or more, as measured according to ASTM D 256 (Method A), optionally to a high of about 30 KJ/m$^2$, about 35 KJ/m$^2$, about 45 KJ/m$^2$, about 55 KJ/m$^2$, or about 65 KJ/m$^2$.

The impact copolymer can have a Gardner impact strength at −30° C. from about 2 KJ/m$^2$ to about 100 KJ/m$^2$, about 3 KJ/m$^2$ to about 80 KJ/m$^2$, or about 4 KJ/m$^2$ to about 60 KJ/m$^2$, as measured according to ASTM D 5420 (GC).

The impact copolymer can have a heat deflection temperature (HDT) of about 80° C. or more, about 85° C. or more, about 90° C. or more, or about 95° C. or more, as measured according to ASTM D 648 (0.45 MPa).

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing polypropylenes or blends thereof, may be used in a variety of end-use applications. Such applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 μm are usually suitable. Films intended for packaging are usually from 10 to 50 μm thick. The thickness of the sealing layer is typically 0.2 to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

In another embodiment, this invention relates to:
1. A metallocene catalyst compound represented by the formula:

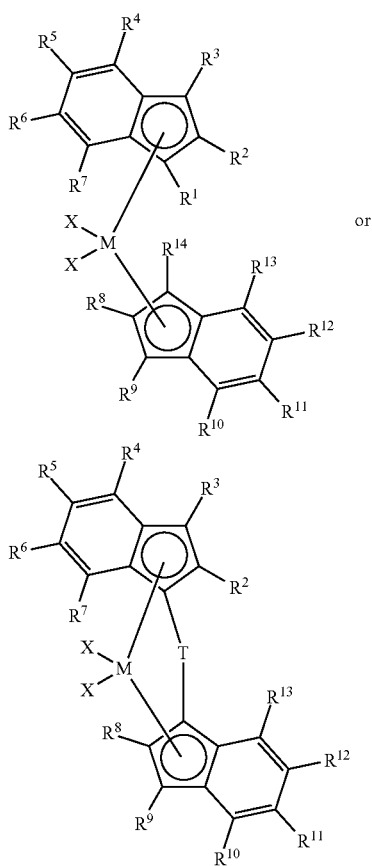

wherein,

R² and R⁸ are not the same;

R⁴ and R¹⁰ are substituted phenyl groups, where at least one of R⁴ and R¹⁰ is a phenyl group substituted at the 3 and 5 position;

M is a group transition 2, 3 or 4 metal;

T is a bridging group;

each X is an anionic leaving group;

each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;

R² is a substituted or unsubstituted $C_3$-$C_{20}$ hydrocarbyl group, where the group is substituted at the alpha position; and R⁸ is a linear $C_1$-$C_{10}$ alkyl group which may be halogenated.

2. The metallocene catalyst of paragraph 1, wherein R² is an alkyl group which is branched in α-position, preferably R² is an isopropyl, sec-butyl, 1-methylbutyl, 1-ethylpropyl, 1-methylpentyl, 1-ethylbutyl, 1-methylhexyl, 1-ethylpentyl, 1-propylbutyl, etc.

3. The metallocene catalyst of either of paragraphs 1 or 2, wherein R⁸ is methyl, ethyl, propyl, butyl, pentyl, hexyl, heptyl, octyl, nonyl or decyl.

4. The metallocene catalyst of either of any of paragraphs 1 through 3, wherein at least one of R⁴ and R¹⁰ is a phenyl group substituted at the 3 and 5 positions with $C_1$ to a $C_{10}$ alkyl groups or aryl groups or combinations thereof.

5. The metallocene catalyst of paragraph 1 to 4, wherein R⁴ and R¹⁰ are independently a phenyl group substituted at the 3 and 5 positions with $C_1$ to a $C_{10}$ alkyl groups or aryl groups or combinations thereof.

6. The metallocene catalyst of any of paragraphs 1 through 5, wherein M is Hf, Ti and/or Zr.

7. The metallocene catalyst of any of paragraphs 1 through 6, wherein each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system).

8. The metallocene catalyst of any of paragraphs 1 through 7, wherein T is represented by the formula $R_2{}^a J$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

9. The metallocene catalyst of any of paragraphs 1 through 7, wherein T is $CH_2$, $CH_2CH_2$, $C(CH_3)_2$, $SiMe_2$, $SiPh_2$, SiMePh, $Si(CH_2)_3$, $Si(CH_2)_4$, $Si(Me_3SiPh)_2$, or $Si(CH_2)_5$.

10. The metallocene catalyst of any of paragraphs 1 through 13, wherein the rac/meso ratio is 10:1 or greater, or 7:1 or greater, or 5:1 or greater.

11. A catalyst system comprising activator and the metallocene compound of any of paragraphs 1 through 10.

12. The catalyst system of paragraph 11, wherein the activator comprises alumoxane.

13. The catalyst system of paragraph 11, wherein alumoxane is present at a molar ratio of aluminum to catalyst compound transition metal of 100:1 or more.

14. The catalyst system of paragraph 11, wherein the activator comprises a non-coordinating anion activator.

15. The catalyst system of paragraph 11, wherein activator is represented by the formula:

$$(Z)_d{}^+(A^{d-})$$

wherein Z is (L-H) or a reducible Lewis Acid, L is an neutral Lewis base; H is hydrogen; (L-H)⁺ is a Bronsted acid; $A^{d-}$ is a non-coordinating anion having the charge d−; and d is an integer from 1 to 3.

16. The catalyst system of paragraph 11, wherein activator is represented by the formula:

$$(Z)_d{}^+(A^{d-})$$

wherein Ad− is a non-coordinating anion having the charge d−; d is an integer from 1 to 3, and Z is a reducible Lewis acid represented by the formula: (Ar3C+), where Ar is aryl or aryl substituted with a heteroatom, a $C_1$ to $C_{40}$ hydrocarbyl, or a substituted $C_1$ to $C_{40}$ hydrocarbyl.

17. The catalyst system of paragraph 11, wherein the activator is one or more of:

N,N-dimethylanilinium tetrakis(pentafluorophenyl)borate,
triphenylcarbenium tetrakis(pentafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(t-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium)tetrakis(perfluoronaphthyl)borate,
tropillium tetrakis(perfluoronaphthyl)borate,
triphenylcarbenium tetrakis(perfluoronaphthyl)borate, triphenylphosphonium tetrakis(perfluoronaphthyl)borate,
triethylsilylium tetrakis(perfluoronaphthyl)borate,
benzene(diazonium)tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(t-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium)tetrakis(perfluorobiphenyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium)tetrakis(perfluorobiphenyl)borate,
[4-t-butyl-PhNMe$_2$H][(C$_6$F$_3$ (C$_6$F$_5$)$_2$)$_4$B],
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium)tetrakis(pentafluorophenyl)borate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium)tetrakis(pentafluorophenyl)borate,
trimethylammonium tetrakis-(2,3,4,6-tetrafluorophenyl)borate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluoro-phenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl)borate,
N,N-dimethyl-(2,4,6-trimethylanilinium)tetrakis-(2,3,4,6-tetrafluorophenyl)borate,
tropillium tetrakis-(2,3,4,6-tetrafluorophenyl)borate,
triphenylcarbenium tetrakis-(2,3,4,6-tetrafluorophenyl)borate,
triphenylphosphonium tetrakis-(2,3,4,6-tetrafluorophenyl)borate,
triethylsilylium tetrakis-(2,3,4,6-tetrafluorophenyl)borate,
benzene(diazonium)tetrakis-(2,3,4,6-tetrafluorophenyl)borate,
trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(t-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium)tetrakis(3,5-bis(trifluoromethyl)phenyl)borate,
tropillium tetrakis(3,5-bis(trifluoromethyl)phenyl)borate,
triphenylcarbenium tetrakis(3,5-bis(trifluoromethyl)phenyl)borate,
triphenylphosphonium tetrakis(3,5-bis(trifluoromethyl)phenyl)borate,
triethylsilylium tetrakis(3,5-bis(trifluoromethyl)phenyl)borate,
benzene(diazonium)tetrakis(3,5-bis(trifluoromethyl)phenyl)borate,
di-(i-propyl)ammonium tetrakis(pentafluorophenyl)borate,
dicyclohexylammonium tetrakis(pentafluorophenyl)borate,
tri(o-tolyl)phosphonium tetrakis(pentafluorophenyl)borate,
tri(2,6-dimethylphenyl)phosphonium tetrakis(pentafluorophenyl)borate,
triphenylcarbenium tetrakis(perfluorophenyl)borate,
1-(4-(tris(pentafluorophenyl)borate)-2,3,5,6-tetrafluorophenyl)pyrrolidinium,
tetrakis(pentafluorophenyl)borate,
4-(tris(pentafluorophenyl)borate)-2,3,5,6-tetrafluoropyridine, and
triphenylcarbenium tetrakis(3,5-bis(trifluoromethyl)phenyl)borate).

18. The catalyst system of paragraphs 11 to 17, wherein the catalyst system is supported.

19. The catalyst system of paragraph 18, wherein the catalyst system is supported on silica.

20. A process to polymerize olefins comprising contacting one or more olefins with a catalyst system comprising an activator and a catalyst compound of any of paragraphs 1 to 10.

21. The process of paragraph 20, wherein the metallocene catalyst or catalyst system is in solution phase producing a polymer having an Mw/Mn of from about 1.7 to about 2.5.

22. The process of paragraph 20, wherein the metallocene catalyst or catalyst system is on a support to produce a polymer having a Mw/Mn from about 2.5 to about 15.

23. The process of paragraph 20, wherein the process occurs at a temperature of from about 0° C. to about 300° C., at a pressure in the range of from about 0.35 MPa to about 10 MPa, and at a time up to 300 minutes.

24. The process of paragraph 23 further comprising obtaining polymer.

EXPERIMENTAL

MAO is methyl alumoxane (30 wt % in toluene) obtained from Albemarle.

EXAMPLES

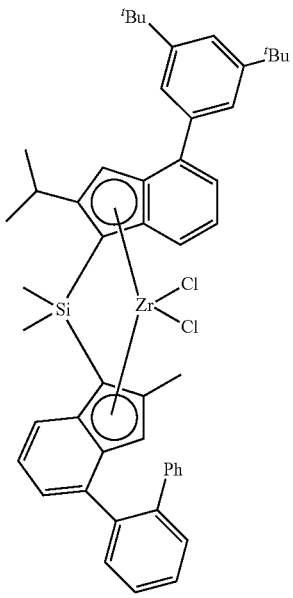

Lithium {1-[4-(3,5-di-test-butylphenyl)-2-isopropyl indenide]}

A solution of 7-(3,5-di-tert-butylphenyl)-2-isopropyl-indene (3.200 g, 9.25 mmol) in diethyl ether (50 mL) (containing residue amounts of THF) was precooled at −35° C. for 0.5 h. "BuLi (2.5 M, 4.3 mL, 10.75 mmol) was added. The solution was stirred at room temperature for 3 h. All volatiles were evaporated. The residue was washed with pentane (50 mL) and dried under vacuum to give the crude lithium compound (3.61 g) (containing 0.4 eq. of pentane and 0.45 eq. of THF).

Chlorodimethyl[4-(3,5-di-tert-butylphenyl)-2-isopropyl-indenyl]silane

A solution of the above crude product (1.5 g, 3.63 mmol) in diethyl ether (20 mL) was precooled at −35° C. for 30 min. Me$_2$SiCl$_2$ (6.97 g, 54.5 mmol) was added and the white slurry was stirred at room temperature for 3 h. All volatiles were evaporated. The residue was extracted with pentane (50 mL) and the filtrate was concentrated to dryness under vacuum to give the product (1.63 g, 99%).

Dimethylsilyl[4-(3,5-di-tert-butylphenyl)-2-isopropyl-indenyl]trifluoromethanesulfonate A solution of chlorodimethyl[4-(3,5-di-tert-butylphenyl)-2-isopropyl-indenyl]silane (1.63 g, 3.60 mmol) in toluene (50 mL) was treated with silver trifluoromethanesulfonate (0.97 g, 3.78 mmol) with stirring. The white slurry was stirred at room temperature for 3 h. Toluene was removed under vacuum and the residue was extracted with pentane (100 mL). The pentane filtrate was concentrated under vacuum to give the product (2.011 g, 99%).

(4-o-Biphenyl-2-methyl-indenyl)(4-(3,5-di-tert-butylphenyl)-2-isopropyl-indenyl)dimethylsilane A precooled solution of dimethylsilyl[4-(3,5-di-tert-butylphenyl)-2-isopropyl-1H-inden-1-yl]trifluoromethanesulfonate (1.0 g, 1.81 mmol) in diethyl ether (25 mL) was added to a precooled mixture of lithium [1-(4-o-biphenyl-2-cm-ethyl indenide)] (0.52 g, 1.81 mmol) in diethyl ether (25 mL). The solution was stirred at room temperature overnight. Diethyl ether was evaporated. The residue was subjected to flash chromatography (silica gel, eluent: hexane/Et$_2$O=100:5) to give the crude product as a colorless foam (1.451 g).

Dilithium dimethylsilyl (4-o-biphenyl-2-methyl indenide) (4-(3,5-di-tert-butylphenyl)-2-isopropyl indenide)

"BuLi (2.5 M, 1.7 mL, 4.31 mmol) was added to a precooled solution of the above product (1.403 g, 2.05 mmol) in diethyl ether (20 mL). The solution was stirred at room temperature for 2 h. All volatiles were removed under vacuum. The residue was washed with pentane (20 mL) and dried under vacuum to give the dilithium compound (1.08 g, 57%, with 1.1 eq. of pentane and 2.1 eq. of diethyl ether).

Dimethylsilyl (4-o-biphenyl-2-methyl-indenyl) (4-(3,5-di-tert-butylphenyl)-2-isopropyl-indenyl) zirconium dichloride A precooled solution of the above [dilithium dimethylsilyl (4-o-biphenyl-2-cyclopropyl indenide) (4-(3,5-di-tert-butylphenyl)-2-methyl indenide)][1.1 eqiv. Pentane and 2.1 equiv. Et$_2$O] (1.08 g, 1.17 mmol) in Et$_2$O (10 mL) was added to a precooled slurry of ZrCl$_4$ (0.268 g, 1.17 mmol) in Et$_2$O (10 mL). The mixture was stirred at room temperature for 3 h. The solution was evaporated to dryness. The residue was extracted with toluene (20 mL). The toluene filtrates were evaporated to dryness and recrystallized (pentane/Et$_2$O=5/2, reflux then cooling to −35° C.) to afford 0.329 g (33%) of the corresponding metallocene with a rac/meso-ratio of <1:50. The combined filtrate was concentrated and recrystallized (pentane/dichloromethane=5/1, reflux then cooling to room temperature) to afford 0.331 g (34%) of dimethylsilyl (4-o-biphenyl-2-methyl-indenyl) (4-(3,5-di-tert-butylphenyl)-2-isopropyl-indenyl) zirconium dichloride with a rac/meso-ratio of >50:1. $^1$H NMR (400 MHz, CD$_2$Cl$_2$, 23° C.), rac-form isomer: δ 7.85-7.76 (m, 1H), 7.65 (d, 1H), 7.55-7.48 (m, 3H), 7.46-7.41 (m, 4H), 7.38 (d, 1H), 7.13-7.02 (m, 7H), 6.99 (s, 1H), 6.94-6.88 (m, 1H), 6.44 (s, 1H), 3.29-3.18 (m, 1H), 2.12 (s, 3H), 1.34 (s, $^t$Bu×2, 18H), 1.33 (s, SiMe, 3H), 1.32 (s, SiMe, 3H), 1.08 (d, 3H), 1.02 (d, 3H). meso-form isomer: δ 7.74-7.69 (m, 1H), 7.70 (d, 1H), 7.59 (d, 1H), 7.48-7.37 (m, 6H), 7.19-7.16 (m, 1H), 7.11-7.05 (m, 3H), 7.04-6.98 (m, 2H), 6.91 (s, 1H), 6.89-6.82 (m, 2H), 6.74-6.69 (m, 1H), 6.36 (s, 1H), 3.18-3.07 (m, 1H), 2.22 (s, 3H), 1.45 (s, SiMe, 3H), 1.39 (d, 3H), 1.34 (s, $^t$Bu×2, 18H), 1.22 (s, SiMe, 3H), 1.14 (d, 3H).

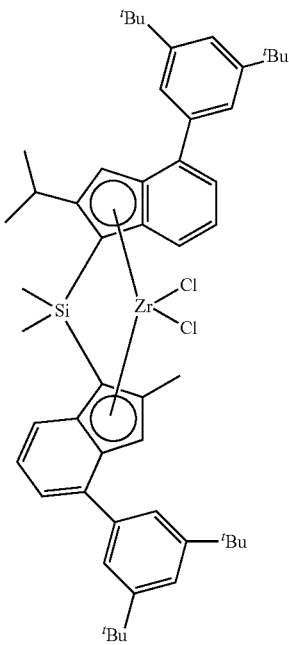

Lithium {1-[4-(3,5-di-tert-butylphenyl)-2-methyl indenide]}

A solution of 4-(3,5-di-tert-butylphenyl)-2-methyl-indene (3.18 g, 10.0 mmol) in diethyl ether (50 mL) was precooled to −30° C. ″BuLi (2.5 M, 4.2 mL, 10.5 mmol) was added. The solution was stirred at room temperature for 3 h. All volatiles were evaporated. The residue was washed with pentane (10 mL×2) and dried under vacuum to give the crude product (3.25 g).

Chlorodimethyl[4-(3,5-di-tert-butylphenyl)-2-methyl-indenyl]silane

A solution of the above crude product (3.25 g, 10.0 mmol) in diethyl ether (50 mL) was precooled to −30° C., and Me$_2$SiCl$_2$ (12.8 g, 100.0 mmol) was added and the white slurry was stirred overnight at room temperature. All volatiles were evaporated. The residue was extracted with hexane (50 mL) and the filtrate was concentrated to dryness under vacuum to give the product (4.16 g).

Dimethylsilyl[4-(3,5-di-tert-butylphenyl)-2-methyl-indenyl]-trifluoromethanesulfonate A solution of chlorodimethyl[4-(3,5-di-tert-butylphenyl)-2-methyl-indenyl]silane (4.16 g, 10.0 mmol) in toluene (30 mL) was added to a solution of silver trifluoromethanesulfonate (2.69 g, 10.5 mmol) in toluene (5 mL) with stirring. The white slurry was stirred at room temperature for 5 h. Toluene was removed under vacuum and the residue was extracted with hexane (100 mL). The pentane filtrate was concentrated under vacuum to give the product (5.308 g).

(4-(3,5-di-tert-butylphenyl)-2-isopropyl-indenyl)(4-(3,5-di-tert-butylphenyl)-2-methyl-indenyl)dimethyl-silane A precooled solution of dimethylsilyl[4-(3,5-di-tert-butyl-phenyl)-2-methyl-1H-inden-1-yl]trifluoromethanesulfonate (2.21 g, 4.3 mmol) in diethyl ether (15 mL) was added to a precooled mixture of above lithium {1-[4-(3,5-di-tert-w butylphenyl)-2-isopropyl indenide]}(pentane)$_{0.4}$(THF)$_{0.45}$ (1.5 g, 3.6 mmol) in diethyl ether (15 mL). The solution was stirred at room temperature overnight. Then diethyl ether was evaporated. The residue was subjected to flash chromatography (silica gel, eluent hexane/dichloromethane 50:1) to yield the product as a colorless foam (2.3 g).

Dilithium dimethylsilyl (4-(3,5-di-tert-butylphenyl)-2-isopropyl indenide) (4-(3,5-di-test-butylphenyl)-2-methyl indenide)

″BuLi (2.5 M, 2.6 mL, 6.55 mmol) was added to a precooled solution of the above product (2.3 g, 3.2 mmol) in diethyl ether (50 mL). The solution was stirred at room temperature for 3 h. All volatiles were removed under vacuum. The residue was washed with pentane (10 mL×2) and dried under vacuum to give the dilithium compound (containing 0.15 eq. of Et$_2$O) (2.36 g).

Dimethylsilyl (4-(3,5-di-tert-butylphenyl)-2-isopropyl-indenyl) (4-(3,5-di-tert-butylphenyl)-2-methyl-indenyl) zirconium dichloride A precooled solution of the above dilithium dimethylsilyl (4-(3,5-di-tert-butylphenyl)-2-isopropyl indenide) (4-(3,5-di-tert-butylphenyl)-2-methyl indenide) (2.36 g, 3.17 mmol) in toluene (50 mL) was treated with ZrCl$_4$ (0.735 g, 3.2 mmol). The mixture was stirred at room temperature overnight. The mixture was filtered to remove the LiCl and the filtrates were concentrated to dryness, the residue was washed with 100 mL of pentane and recrystallized (diethyl ether/hexane=1:1, reflux then cooling to room temperature) to give 0.413 g (14.7%) of dimethylsilyl (4-o-biphenyl-2-cyclopropyl-indenyl) (4-(3,5-di-tert-butylphenyl)-2-methyl-indenyl) zirconium dichloride with a rac/meso ratio of 1:15. Then the mother liquor war concentrated and recrystallized (toluene/hexane=1:8, reflux then cooling to room temperature) to give 0.105 g (3.7%) of (4-(3,5-di-tert-butylphenyl)-2-isopropyl-indenyl) (4-(3,5-di-tert-butylphenyl)-2-methyl-indenyl) zirconium dichloride with a rac/meso ratio of 10:1. $^1$H NMR (400 MHz, CD$_2$Cl$_2$, 23° C.), rac-form isomer: δ 7.75 (d, 1H), 7.66 (d, 1H), 7.63-7.56 (m, 4H), 7.48-7.38 (m, 4H), 7.18-7.11 (m, 2H), 7.06 (s, 1H), 6.93 (s, 1H), 3.29 (m, 1H), 2.29 (s, 3H), 1.43-1.30 (m, $^t$Bu×4 overlapped with SiMe$_2$, 42H), 1.14 (d, 3H), 1.07 (d, 3H). meso-form isomer: δ 7.74-7.68 (m, 2H), 7.55-7.51 (m, 4H), 7.46-7.42 (m, 2H), 7.20-7.16 (m, 2H), 6.99 (s, 1H), 6.96-6.89 (m, 2H), 6.86 (s, 1H), 3.30-3.18 (m, 1H), 2.41 (s, 3H), 1.53 (s, 3H, SiMe), 1.47 (d, 3H), 1.37 (s, 18H, 13u×2), 1.35 (s, 18H, 13u×2), 1.31 (s, 3H, SiMe), 1.19 (d, 3H).

Supported Dimethylsilyl (4-o-biphenyl-2-cyclopropyl-indenyl) (4-(3,5-di-tert-butylphenyl)-2-methyl-indenyl) Zirconium Dichloride (Catalyst C)

In a 20 mL vial the metallocene (19.4 mg, 0.0230 mmol) was stirred alongside MAO (30% by weight in toluene, 0.2125 g of solution) along with another 2 mL of toluene for 1 h. In a small celstir 130° C. calcined silica pretreated with MAO (130° C. SMAO) (0.5747 g) was slurried in 20 mL of toluene. The celstir was chilled for 1 min in the freezer before the catalyst solution is added to the slurry. The slurry was stirred for 1 h while spending 1 min of every 10 min in the freezer. The slurry is then heated to 40° C. and stirred for 2 h. The slurry was then filtered, reslurried in 20 mL of toluene and stirred for an additional 30 min at 60° C. The slurry was then filtered, reslurried in 20 mL of toluene and stirred for an additional 30 min at 60° C. The slurry was then filtered, reslurried in 20 mL of toluene and stirred for an additional 30 min at 60° C. and then filtered for the final time. The celstir was washed out with 20 mL of toluene and the solid was dried under vacuum. Collected 0.5044 g of pink solid. The SMAO is typically prepared as follows: 130° C. Calcined Davison 948 Silica (20.8606 g, calcined at 130° C.) was slurried in 121 mL of toluene and chilled in the freezer (approx. −35° C.). MAO (50.5542 g of a 30% wt solution in toluene) was added slowly in 3 parts with the silica slurry returned to the freezer for approx. 2 minutes between additions. The slurry was stirred at room temperature for 2 h, filtered with a glass frit filter, reslurried in 80 mL of toluene for 15 min at room temperature, and then filtered again. The solid was reslurried in 80 mL of toluene at 80° C. for 30 min and then filtered. The solid was reslurried in 80 mL of toluene at 80° C. for 30 min and then filtered a final time. The celstir and solid were washed out with 40 mL of toluene. The solid was then washed with pentane and dried under vacuum for 24 h. Collected 28.9406 g of a free flowing white powder.

Supported Dimethylsilyl (4-o-Biphenyl-2-(1-methylcyclohexyl)methyl-indenyl) (4-(3,5-di-tert-butylphenyl)-2-methyl-indenyl) Zirconium Dichloride (Catalyst D)

In a 20 mL vial the metallocene (25.6 mg, 0.0280 mmol) was stirred alongside MAO (30% by weight in toluene, 0.2410 g of solution) along with another 2 mL of toluene for 1 h 20 min. In a small celstir MS-3050-S*MAO was slurried in 20 mL of toluene. The catalyst was added to the slurry and stirred for 1 h 10 min. The slurry is filtered and washed 4 times with 20 mL of toluene. The solid was dried under vacuum. Collected 0.6355 g of pink solid. The S*MAO is typically prepared as follows: In a celstir MS-3050 (600° C. calcined, 8.8627 g) was slurried in 90 mL of toluene. MAO (25.9320 g of a 30% wt toluene solution) was added slowly to the slurry. The slurry was stirred at room temperature for 1 h and then 80° C. for 20 min. Reaction monitoring via NMR showed high MAO uptake. An additional 2.8644 g of the MAO solution was added to the slurry and stirred for another 20 min. NMR analysis showed full saturation of silica by the MAO. The slurry was filtered with a glass frit filter and washed three times with 25 mL of toluene and one time with 40 mL of toluene. The solid was dried under vacuum for 24 h. 15.0335 g of a free flowing white solid were collected.

Supported Dimethylsilyl (4-o-biphenyl-2-methyl-indenyl) (4-(3,5-di-tert-butylphenyl)-2-isopropyl-indenyl) zirconium dichloride (Catalyst E)

In a 20 mL vial the metallocene (32 mg, 0.038 mmol) was stirred alongside MAO (30% by weight in toluene, 0.3304 g of solution) along with another 3 mL of toluene for 1 h. In a small celstir 130° C. calcined silica pretreated with MAO (130° C. SMAO) (0.9486 g) was slurried in 20 mL of toluene. The celstir was chilled for 15 min in the freezer (−35° C.). The catalyst solution was added to the slurry and stirred for 1 hr. The slurry was placed in the freezer every a few minutes. The slurry was then heated to 40° C. and stirred for 2 h. The slurry was then filtered, reslurried in 20 mL of toluene and stirred for an additional 30 min at 60° C. The slurry was then filtered, reslurried in 20 mL of toluene and stirred for an additional 30 min at 60° C. The slurry was then filtered, reslurried in 20 mL of toluene and stirred for an additional 30 min at 60° C. and then filtered for the final time. The celstir was washed out with 20 mL of toluene. The solid was washed with pentane and dried under vacuum overnight. Collect 0.8256 g of pink solid.

Supported Dimethylsilyl (4-(3,5-di-tert-butylphenyl)-2-isopropyl-indenyl) (4-(3,5-di-tert-butylphenyl)-2-methyl-indenyl) zirconium dichloride (Catalyst F)

In a 20 mL vial the metallocene (22.5 mg, 0.0255 mmol) was stirred alongside MAO (30% by weight in toluene, 0.2130 g of solution) along with another 2 mL of toluene for 1 h. In a small celstir 130° C. calcined silica pretreated with MAO (130° C. SMAO) (0.6392 g) was slurried in 20 mL of toluene. The catalyst solution was added to the slurry and stirred for 1 hr. The slurry was placed in the freezer every a few minutes. The slurry was then heated to 40° C. and stirred for 2 h. The slurry was then filtered, reslurried in 20 mL of toluene and stirred for an additional 30 min at 60° C. The slurry was then filtered, reslurried in 20 mL of toluene and stirred for an additional 30 min at 60° C. The slurry was then filtered, reslurried in 20 mL of toluene and stirred for an additional 30 min at 60° C. and then filtered for the final time. The celstir was washed out with 20 mL of toluene. The solid was washed with pentane and dried under vacuum overnight. Collect 0.5215 g of pink solid.

Supported rac-[(2,2'-Biphenylsilylene)bis(2-isopropyl-4-(3,5-di-t-butyl)phenylindenyl)]dimethylzirconium (Catalyst G)

In a 20 mL vial the metallocene (41.3 mg, 0.0417 mmol) was stirred alongside MAO (30% by weight in toluene, 0.4048 g of solution) along with another 2 mL of toluene for 1 h. In a small celstir 130° C. calcined silica pretreated with MAO (130° C. SMAO) (1.0470 g) was slurried in 20 mL of toluene. The catalyst solution was added to the slurry and stirred for 1 h. The slurry was placed in the freezer every a few minutes. The slurry was then heated to 40° C. and stirred for 2 h. The slurry was then filtered, reslurried in 20 mL of toluene and stirred for an additional 30 min at 60° C. The slurry was then filtered, reslurried in 20 mL of toluene and stirred for an additional 30 min at 60° C. The slurry was then filtered, reslurried in 20 mL of toluene and stirred for an additional 30 min at 60° C. and then filtered for the final time. The celstir was washed out with 20 mL of toluene. The solid was washed with pentane and dried under vacuum overnight. Collected 0.9790 g of pink solid.

General Procedure for Small Scale Solution Polymerization

Unless stated otherwise propylene homopolymerizations and ethylene-propylene copolymerizations (if any) were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pp. 4306-4317, each of which is fully incorporated herein by reference for US purposes. Although the specific quantities, temperatures, solvents, reactants, reactant ratios, pressures, and other variables may have changed from one polymerization run to the next, the following describes a typical polymerization performed in a parallel, pressure reactor.

Propylene Polymerization with Metallocene

A pre-weighed glass vial insert and disposable stirring paddle were fitted to each reaction vessel of the reactor, which contains 48 individual reaction vessels. The reactor was then closed and propylene (typically 1 mL) was introduced to each vessel as a condensed gas liquid (typically 1 mL) (as shown in examples in Table 1) or gas (as shown in examples in Table 3). Then solvent (typically isohexane)

was added to bring the total reaction volume, including the subsequent additions, to 5 mL and the reactor vessels were heated to their set temperature (usually between 50° C. and 110° C.).

The contents of the vessel were stirred at 800 rpm. An activator solution (typically 100-1000 molar equivalents of methyl alumoxane (MAO) in toluene) was then injected into the reaction vessel along with 500 microliters of toluene, followed by a toluene solution of catalyst (typically 0.50 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a predetermined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

Ethylene Propylene Copolymerization with Supported Catalyst

A pre-weighed glass vial insert and disposable stirring paddle were fitted to each reaction vessel of the reactor, which contains 48 individual reaction vessels. The reactor was then closed and propylene gas was introduced to each vessel to purge the nitrogen out of the system. If any modules receive Hydrogen, it is added in now during the purge process. The solvent (typically isohexane) is added next according to the set total reaction volume, including the following additions, to 5 mL usually. At this time scavenger and/or co-catalyst and/or a chain transfer agent, such as tri-n-octylaluminum in toluene (typically 100-1000 nmol) was added. The contents of the vessels are now stirred at 800 rpm. The propylene in now added as gas to a set pressure. Now the reactor vessels are heated to their set run temperature (usually between 50° C. and 110° C.). The ethylene is now added as a comonomer and it will be added as a gas to a pre-determined pressure (typically 10-100 psi) above the pressure of the propylene while the reactor vessels were heated to a set run temperature.

The slurry catalysts are vortexed to suspend the catalyst particles into a solution. The buffer toluene (typically 100 microliters), the toluene solution of catalyst (typically 3 mg/ml concentration), and another aliquot of toluene (500 microliters) is injected into the reactors now.

The reaction was then allowed to proceed until a predetermined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector (as shown in examples in Table 2) or Polymer Char IR4 detector (as shown in examples in Table 3 and Table 4). The molecular weights presented are relative to linear polystyrene standards and are uncorrected.

Differential Scanning calorimetry (DSC) (DSC Procedure-1) measurements were performed on a TA-Q200 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

The amount of ethylene incorporated in the polymers (weight %) was determined by rapid FT-IR spectroscopy on a Bruker Vertex 70 IR in reflection mode. Samples were prepared in a thin film format by evaporative deposition techniques. Weight percent ethylene was obtained from the ratio of peak heights at 729.8 and 1157.9 cm-1. This method was calibrated using a set of ethylene/propylene copolymers with a range of known wt % ethylene content.

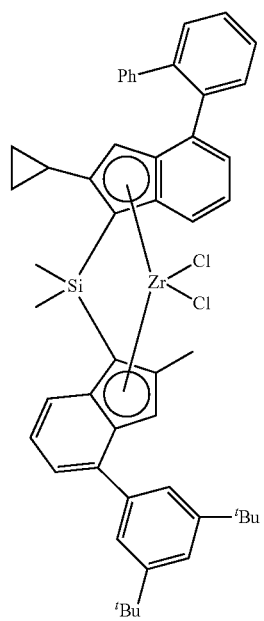

MTC-1
rac/meso = 33/1

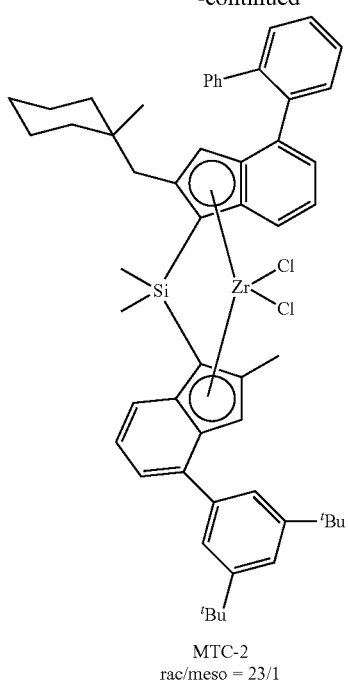
MTC-2
rac/meso = 23/1
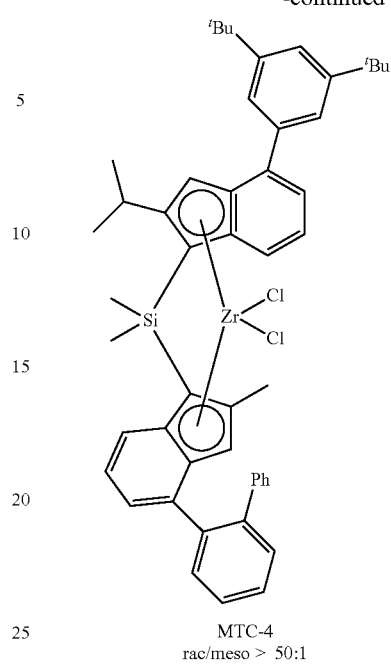
MTC-4
rac/meso > 50:1
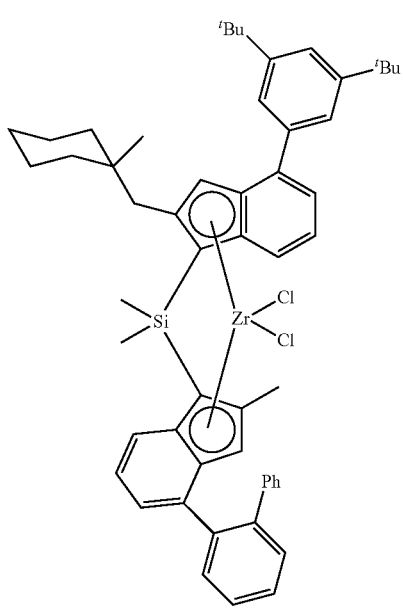
MTC-3
rac/meso = 1.3/1
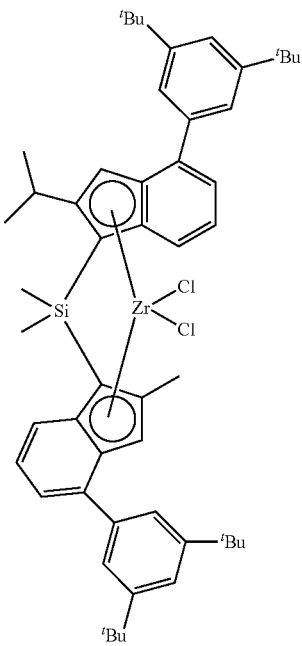
MTC-5
rac/meso = 10/1

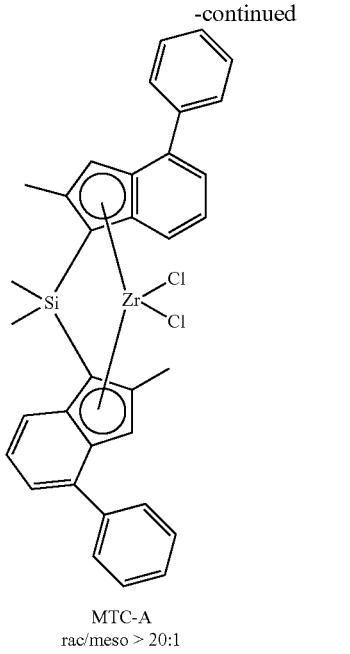

MTC-A
rac/meso > 20:1

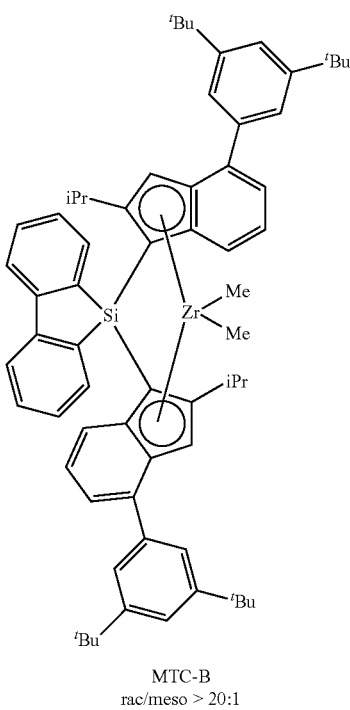

MTC-B
rac/meso > 20:1

TABLE 1

Small Scale Solution Propylene Polymerization Using MTC-1, MTC-2, MTC-3, MTC-A and MAO. Conditions: isohexane solvent, propylene (as a condensed gas liquid) added = 1 mL, total volume = 5 mL.

| Ex. # | MTC | MTC (μmol) | MAO/MTC (molar) | Polym Temp (° C.) | Quench Time (s) | Yield (mg) | Activity (g/mmol·hr) |
|---|---|---|---|---|---|---|---|
| 1 | MTC-1 | 0.025 | 500 | 70 | 84 | 241 | 413143 |
| 2 | MTC-1 | 0.025 | 500 | 70 | 89 | 222 | 359191 |
| 3 | MTC-1 | 0.025 | 500 | 70 | 91 | 252 | 398769 |
| 4 | MTC-2 | 0.025 | 500 | 70 | 190 | 165 | 125053 |
| 5 | MTC-2 | 0.025 | 500 | 70 | 244 | 185 | 109180 |
| 6 | MTC-2 | 0.025 | 500 | 70 | 226 | 177 | 112779 |
| 7 | MTC-3 | 0.025 | 500 | 70 | 109 | 148 | 195127 |
| 8 | MTC-3 | 0.025 | 500 | 70 | 168 | 158 | 135257 |
| 9 | MTC-3 | 0.025 | 500 | 70 | 131 | 204 | 224574 |
| 10 | MTC-A | 0.025 | 500 | 70 | 77 | 188 | 351584 |
| 11 | MTC-A | 0.025 | 500 | 70 | 96 | 212 | 318000 |
| 12 | MTC-A | 0.025 | 500 | 70 | 96 | 208 | 312000 |
| 13 | MTC-A | 0.025 | 500 | 70 | 90 | 185 | 296480 |
| 14 | MTC-A | 0.025 | 500 | 70 | 104 | 213 | 295477 |
| 15 | MTC-A | 0.025 | 500 | 70 | 92 | 163 | 254661 |
| 16 | MTC-1 | 0.025 | 500 | 100 | 64 | 160 | 360000 |
| 17 | MTC-1 | 0.025 | 500 | 100 | 70 | 170 | 349714 |
| 18 | MTC-1 | 0.025 | 500 | 100 | 71 | 157 | 318423 |
| 19 | MTC-2 | 0.025 | 500 | 100 | 124 | 104 | 120774 |
| 20 | MTC-2 | 0.025 | 500 | 100 | 140 | 109 | 112114 |
| 21 | MTC-2 | 0.025 | 500 | 100 | 141 | 116 | 118468 |
| 22 | MTC-3 | 0.025 | 500 | 100 | 84 | 111 | 189943 |
| 23 | MTC-3 | 0.025 | 500 | 100 | 92 | 123 | 192209 |
| 24 | MTC-3 | 0.025 | 500 | 100 | 96 | 136 | 203250 |
| 25 | MTC-A | 0.025 | 500 | 100 | 65 | 145 | 321231 |
| 26 | MTC-A | 0.025 | 500 | 100 | 68 | 138 | 292235 |
| 27 | MTC-A | 0.025 | 500 | 100 | 66 | 121 | 264000 |
| 28 | MTC-A | 0.025 | 500 | 100 | 58 | 124 | 307366 |
| 29 | MTC-A | 0.025 | 500 | 100 | 61 | 118 | 279502 |
| 30 | MTC-A | 0.025 | 500 | 100 | 66 | 126 | 275782 |

TABLE 2

Small Scale Propylene Polymerization Polymer Characteristics

| Ex. # | MTC | Polym Temp (° C.) | $T_m$ (° C.) | $M_n$ (kg/mol) | $M_w$ (kg/mol) | Mw/Mn |
|---|---|---|---|---|---|---|
| 1 | MTC-1 | 70 | 156.9 | 176 | 311 | 1.8 |
| 2 | MTC-1 | 70 | 156.4 | 182 | 318 | 1.7 |
| 3 | MTC-1 | 70 | 157.2 | 190 | 331 | 1.7 |
| 4 | MTC-2 | 70 | 159.3 | 466 | 751 | 1.6 |
| 5 | MTC-2 | 70 | 160.2 | 430 | 718 | 1.7 |
| 6 | MTC-2 | 70 | 160.0 | 450 | 742 | 1.6 |
| 7 | MTC-3 | 70 | 157.7 | 312 | 534 | 1.7 |
| 8 | MTC-3 | 70 | 157.3 | 374 | 657 | 1.8 |
| 9 | MTC-3 | 70 | 159.7 | 251 | 462 | 1.8 |
| 10 | MTC-A | 70 | 155.5 | 159 | 261 | 1.6 |
| 11 | MTC-A | 70 | 155.2 | 154 | 259 | 1.7 |
| 12 | MTC-A | 70 | 156.5 | 181 | 294 | 1.6 |
| 13 | MTC-A | 70 | 155.5 | 193 | 309 | 1.6 |
| 14 | MTC-A | 70 | 156.0 | 183 | 309 | 1.7 |
| 15 | MTC-A | 70 | 155.8 | 237 | 367 | 1.5 |
| 16 | MTC-1 | 100 | 154.5 | 73 | 116 | 1.6 |
| 17 | MTC-1 | 100 | 153.4 | 71 | 114 | 1.6 |
| 18 | MTC-1 | 100 | 153.9 | 74 | 118 | 1.6 |
| 19 | MTC-2 | 100 | 157.1 | 134 | 204 | 1.5 |
| 20 | MTC-2 | 100 | 158.7 | 128 | 196 | 1.5 |
| 21 | MTC-2 | 100 | 158.6 | 122 | 188 | 1.5 |
| 22 | MTC-3 | 100 | 153.2 | 74 | 131 | 1.8 |
| 23 | MTC-3 | 100 | 153.5 | 73 | 129 | 1.7 |
| 24 | MTC-3 | 100 | 153.2 | 75 | 129 | 1.7 |
| 25 | MTC-A | 100 | 150.1 | 52 | 82 | 1.6 |
| 26 | MTC-A | 100 | 150.6 | 54 | 85 | 1.6 |
| 27 | MTC-A | 100 | 150.1 | 55 | 85 | 1.5 |
| 28 | MTC-A | 100 | 150.6 | 60 | 93 | 1.6 |
| 29 | MTC-A | 100 | 150.9 | 55 | 89 | 1.6 |
| 30 | MTC-A | 100 | 150.4 | 51 | 83 | 1.6 |

TABLE 3

Small Scale Solution Propylene Polymerization Using 0.025 μmol of Catalysts and 500 molar equivalents of MAO. Conditions: isohexane solvent, propylene (introduced to each vessel as gas) added = 9.553 mmol, total volume = 5 mL.

| Ex. # | Catalyst | Tp (°C.) | Quench Time (s) | Yield (mg) | Activity (g/mmol · hr) | Tm (°C.) | Mw (k) | Mw/Mn |
|---|---|---|---|---|---|---|---|---|
| 31 | MTC-1 | 70 | 75 | 258.2 | 495744 | 156.5 | 338 | 2.6 |
| 32 | MTC-1 | 70 | 77 | 274.6 | 513538 | 156.2 | 357 | 2.9 |
| 33 | MTC-4 | 70 | 122 | 120.9 | 142702 | 157.6 | 156 | 1.8 |
| 34 | MTC-4 | 70 | 133 | 122.2 | 132307 | 157.2 | 153 | 1.6 |
| 35 | MTC-5 | 70 | 138 | 93.1 | 97148 | 157.2 | 395 | 1.9 |
| 36 | MTC-5 | 70 | 177 | 74.5 | 60610 | 157.0 | 468 | 1.9 |
| 37 | MTC-A | 70 | 73 | 192.3 | 379332 | 155.3 | 329 | 2.1 |
| 38 | MTC-A | 70 | 70 | 209.1 | 430149 | 155.2 | 330 | 2.2 |
| 39 | MTC-B | 70 | 570 | 50.9 | 12859 | 157.1 | 366 | 1.8 |
| 40 | MTC-1 | 100 | 54 | 156.8 | 418133 | 153.3 | 124 | 2.1 |
| 41 | MTC-1 | 100 | 63 | 147.8 | 337829 | 153.0 | 129 | 1.8 |
| 42 | MTC-4 | 100 | 120 | 81.6 | 97920 | 144.7 | 31 | 1.8 |
| 43 | MTC-4 | 100 | 129 | 93.5 | 104372 | 144.9 | 32 | 1.6 |
| 44 | MTC-5 | 100 | 116 | 64.9 | 80566 | 149.9 | 104 | 2.2 |
| 45 | MTC-5 | 100 | 114 | 61.8 | 78063 | 149.5 | 102 | 1.9 |
| 46 | MTC-A | 100 | 58 | 123.7 | 307117 | 149.9 | 98 | 2.0 |
| 47 | MTC-A | 100 | 52 | 117.5 | 325385 | 150.6 | 96 | 1.9 |

TABLE 4

Small Scale Ethylene Propylene Copolymerization Using Supported Catalysts. Conditions: isohexane solvent, propylene (introduced to each vessel as gas) added = 9.553 mmol, TONAL = 0.4 μmol, total volume = 5 mL.

| | Quench Time(s) | Yield (mg) | gPolymer/ gcat-sup · hr | Mw (k) | Mw/Mn | C2 wt % |
|---|---|---|---|---|---|---|
| Catalyst C | 1070 | 116.7 | 1007 | 258 | 2.1 | 11.5 |
| | 417 | 107.8 | 2386 | 169 | 2.2 | 18.8 |
| | 216 | 135.2 | 5778 | 196 | 2.0 | 28.3 |
| | 281 | 103.2 | 3390 | 238 | 1.9 | 33.1 |
| | 832 | 118.5 | 1315 | 244 | 2.2 | 11.6 |
| | 313 | 125.4 | 3698 | 174 | 2.2 | 17.6 |
| Catalyst E | 2702 | 45.4 | 155 | 256 | 1.9 | 11.7 |
| | 2702 | 65.8 | 225 | 443 | 2.4 | 35.4 |
| | 553 | 90.5 | 1511 | 400 | 2.7 | 26.0 |
| | 2703 | 40.2 | 137 | 545 | 2.2 | 32.5 |
| | 2701 | 32.9 | 112 | 231 | 2.4 | 12.2 |
| | 1320 | 105 | 734 | 295 | 2.2 | 18.3 |
| | 532 | 96 | 1666 | 360 | 2.0 | 23.7 |
| | 2700 | 77.2 | 264 | 506 | 2.2 | 29.6 |
| Catalyst G | 2701 | 33.6 | 115 | 391 | 2.0 | 16.3 |
| | 2703 | 41.9 | 143 | 473 | 2.1 | 21.6 |
| | 2700 | 46.6 | 159 | 651 | 1.9 | 35.8 |
| | 2702 | 45.2 | 154 | 934 | 1.9 | 39.7 |
| | 2700 | 25.1 | 86 | 448 | 1.8 | 16.0 |
| | 2703 | 23.5 | 80 | 581 | 1.7 | 27.0 |
| | 2704 | 26.4 | 90 | 732 | 1.8 | 32.8 |
| | 2700 | 38.5 | 132 | 978 | 2.0 | 30.7 |

General Procedure for Reactor Propylene Polymerization

Supported catalyst (ca. 0.5-0.6 g) was slurried into dry HYDROBRITE™ oil to yield a slurry that contains 5% by weight of supported catalyst. The supported catalysts were added to the reactor as a slurry in oil. The catalyst slurry containing certain amounts of catalysts (see Table 5) was injected using 250 mL propylene into a 2 L autoclave reactor containing propylene (1000 mL) (total propylene 1250 mL), $H_2$ (provided from a 183 mL container under the pressure indicated in the table) and tri-n-octylaluminum, 1.0 mls of a 4.76 vol % hexane solution, at ambient temperature for 5 minutes. Subsequently, the reactor temperature was raised to 70° C. and the polymerization was run for an allotted period of time typically 50 minutes. After the allotted time the reactor was cooled to room temperature and vented.

Gel Permeation Chromatography-DRI (GPC DRI)

Mw, Mn and Mw/Mn are determined by using a High Temperature Gel Permeation Chromatography (Polymer Laboratories), equipped with a differential refractive index detector (DRI). Three Polymer Laboratories PLgel 10 μm Mixed-B columns are used. The nominal flow rate is 1.0 mL/min, and the nominal injection volume is 300 μL. The various transfer lines, columns, and differential refractometer (the DRI detector) are contained in an oven maintained at 160° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the GPC instrument. Polymer solutions are prepared by placing dry polymer in glass vials, adding the desired amount of TCB, then heating the mixture at 160° C. with continuous shaking for about 2 hours. All quantities are measured gravimetrically. The injection concentration is from 0.5 to 2.0 mg/ml, with lower concentrations being used for higher molecular weight samples. Prior to running each sample the DRI detector is purged. Flow rate in the apparatus is then increased to 1.0 ml/minute, and the DRI is allowed to stabilize for 8 hours before injecting the first sample. The molecular weight is determined by combining universal calibration relationship with the column calibration which is performed with a series of monodispersed polystyrene (PS) standards. The MW is calculated at each elution volume with following equation.

$$\log M_X = \frac{\log(K_X/K_{PS})}{a_X + 1} + \frac{a_{PS} + 1}{a_X + 1} \log M_{PS}$$

where the variables with subscript "X" stand for the test sample while those with subscript "PS" stand for PS. In this method, $a_{PS}$=0.67 and $K_{PS}$=0.000175 while $a_X$ and $K_X$ are obtained from published literature. Specifically, a/K=0.695/0.000579 for PE and 0.705/0.0002288 for PP.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. Specifically, dn/dc=0.109 for both PE and PP.

The mass recovery is calculated from the ratio of the integrated area of the concentration chromatography over elution volume and the injection mass which is equal to the pre-determined concentration multiplied by injection loop volume.

All molecular weights are reported in g/mol unless otherwise noted. In event of conflict between the GPC-DRI procedure and the "Rapid GPC," the GPC-DRI procedure immediately above shall be used.

Differential Scanning Calorimetry (DSC)-Procedure-2

Peak crystallization temperature ($T_c$) and peak melting temperature ($T_m$) were measured via Differential Scanning calorimetry using a DSCQ200 unit. The sample was first equilibrated at 25° C. and subsequently heated to 220° C. using a heating rate of 10° C./min (first heat). The sample was held at 220° C. for 3 min. The sample was subsequently cooled down to −100° C. with a constant cooling rate of 10° C./min (first cool). The sample was equilibrated at −100° C. before being heated to 220° C. at a constant heating rate of 10° C./min (second heat). The exothermic peak of crystallization (first cool) was analyzed using the TA Universal Analysis software and the corresponding to 10° C./min cooling rate was determined. The endothermic peak of melting (second heat) was also analyzed using the TA Universal Analysis software and the peak melting temperature ($T_m$) corresponding to 10° C./min heating rate was determined. In event of conflict between the DSC Procedure-1 and DSC procedure-2, DSC procedure-2 shall be used.

Melt Flow Rate (MFR)

MFR was measured as per ASTM D1238, condition L, at 230° C. and 2.16 kg load using a melt indexer.

1% Secant Flexural Modulus

The 1% Secant flexural modulus is measured using an ISO 37-Type 3 bar, with a crosshead speed of 1.0 mm/min and a support span of 30.0 mm using an Instron machine according to ASTM D 790 (A, 1.0 mm/min).

TABLE 5

Propylene Polymerization Using Silica-Supported Catalysts (70° C.)

| Entry | Catalyst | Catalyst Amount (mg) | $H_2$ Pressure (psi) | Yield (g) | Activity (g polymer/ g cat) | MFR (dg/min) | $M_w$ (kg/mol) | Mw/Mn | $T_m$ (° C.) | 1% Secant flexural Modulus (MPa) |
|---|---|---|---|---|---|---|---|---|---|---|
| 1 | Catalyst C | 76 | 0 | 46.26 | 609 | 0.13 | 876 | 9.1 | 152.4 | 1706 |
| 2 | Catalyst C | 76 | 0 | 94.58 | 1244 | 0.13 | 716 | 4.7 | 153.3 | 1767 |
| 3 | Catalyst C | 76 | 0 | 93.91 | 1236 | 0.29 | 717 | 5.3 | 152.9 | 1702 |
| 4 | Catalyst C | 79 | 6 | 119.89 | 1518 | 16 | 319 | 7.2 | 153.1 | 1578 |
| 5 | Catalyst C | 78 | 9 | 146.24 | 1875 | 26 | 238 | 4.1 | 153.1 | 1363 |
| 6 | Catalyst C | 75 | 25 | 226.78 | 3024 | 711 | 125 | 3.6 | 153.0 | 1384 |
| 7 | Catalyst D | 64 | 7 | 130.88 | 2045 | 16 | 217 | 2.2 | 156.6 | 1249 |
| 8 | Catalyst D | 64 | 10 | 144.62 | 2260 | 31 | 176 | 3.8 | 156.8 | 1210 |
| 9 | Catalyst D | 64 | 15 | 157.63 | 2463 | 68 | 148 | 2.4 | 156.6 | 1222 |

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

The invention claimed is:

1. A metallocene catalyst compound represented by the formula:

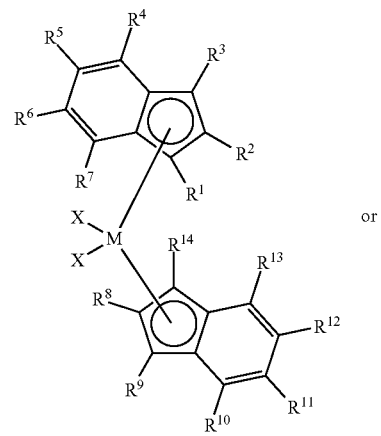

or

-continued

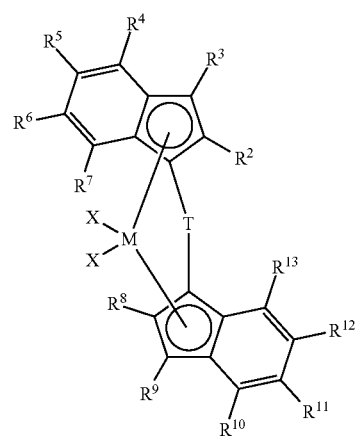

$R^2$ and $R^8$ are not the same;

$R^4$ and $R^{10}$ are substituted phenyl groups, where: both of $R^4$ and $R^{10}$ are a phenyl group substituted at the 3 and 5 positions, or one of $R^4$ and $R^{10}$ is a phenyl group substituted at the 3 and 5 positions and the other is a phenyl group substituted at the 2 position with an aryl group;

M is a group transition 2, 3 or 4 metal;

T is a bridging group;

each X is an anionic leaving group;

each $R^1$, $R^5$, $R^6$, $R^7$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;

$R^2$ is a substituted or unsubstituted $C_3$-$C_{20}$ hydrocarbyl group, where the group is substituted at the alpha position;

$R^3$ and $R^9$ are hydrogen; and $R^8$ is a linear $C_1$-$C_{10}$ alkyl group which is optionally halogenated, wherein the metallocene catalyst compound is a mixture of rac/meso isomers and the rac/meso ratio is 10:1 or greater.

2. The metallocene catalyst compound of claim 1, wherein $R^2$ is an alkyl group which is branched in α-position.

3. The metallocene catalyst compound of claim 1, wherein $R^8$ is methyl, ethyl, propyl, butyl, pentyl, hexyl, heptyl, octyl, nonyl or decyl.

4. The metallocene catalyst compound of claim 1, wherein the 3 and 5 positions are substituted with $C_1$ to $C_{10}$ alkyl groups or aryl groups or combinations thereof.

5. The metallocene catalyst compound of claim 1, wherein $R^4$ and $R^{10}$ are independently a phenyl group substituted at the 3 and 5 positions with $C_1$ to a $C_{10}$ alkyl groups or aryl groups or combinations thereof.

6. The metallocene catalyst compound of claim 1, wherein M is Hf, Ti and/or Zr.

7. The metallocene catalyst compound of claim 1, wherein each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, or two X's optionally form a part of a fused ring or a ring system.

8. The metallocene catalyst compound of claim 1, wherein T is represented by the formula $R^a{}_2J$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ optionally form a cyclic structure including aromatic, partially saturated, or saturated cyclic or fused ring system.

9. The metallocene catalyst compound of claim 1, wherein T is $CH_2$, $CH_2CH_2$, $C(CH_3)_2$, $SiMe_2$, $SiPh_2$, SiMePh, $Si(CH_2)_3$, $Si(CH_2)_4$, $Si(Me_3SiPh)_2$, or $Si(CH_2)_5$.

10. The metallocene catalyst compound of claim 1, wherein the metallocene catalyst compound is a mixture of rac/meso isomers and the rac/meso ratio is 40:1 or greater.

11. A catalyst system comprising activator and the metallocene catalyst compound of claim 1.

12. The catalyst system of claim 11, wherein the activator comprises alumoxane.

13. The catalyst system of claim 11, wherein alumoxane is present at a molar ratio of aluminum to catalyst compound transition metal of 100:1 or more.

14. The catalyst system of claim 11, wherein the activator comprises a non-coordinating anion activator.

15. The catalyst system of claim 11, wherein activator is represented by the formula:

$$(Z)_d{}^+(A^{d-})$$

wherein Z is (L-H) or a reducible Lewis Acid, L is an neutral Lewis base; H is hydrogen; $(L-H)^+$ is a Bronsted acid; $A^{d-}$ is a non-coordinating anion having the charge d-; and d is an integer from 1 to 3.

16. The catalyst system of claim 11, wherein activator is represented by the formula:

$$(Z)_d{}^+(A^{d-})$$

wherein Ad– is a non-coordinating anion having the charge d-; d is an integer from 1 to 3, and Z is a reducible Lewis acid represented by the formula: (Ar3C+), where Ar is aryl or aryl substituted with a heteroatom, a $C_1$ to $C_{40}$ hydrocarbyl, or a substituted $C_1$ to $C_{40}$ hydrocarbyl.

17. The catalyst system of claim 11, wherein the activator is one or more of:

N,N-dimethylanilinium tetrakis(pentafluorophenyl)borate,
triphenylcarbenium tetrakis(pentafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(t-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium)tetrakis(perfluoronaphthyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium)tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(t-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium)tetrakis(perfluorobiphenyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium)tetrakis(perfluorobiphenyl)borate,
[4-t-butyl-PhNMe$_2$H][(C$_6$F$_3$(C$_6$F$_5$)$_2$)$_4$B],
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate, tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium)tetrakis(pentafluorophenyl)borate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium)tetrakis(pentafluorophenyl)borate,
trimethylammonium tetrakis-(2,3,4,6-tetrafluorophenyl)borate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluorophenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl)borate,
N,N-dimethyl-(2,4,6-trimethylanilinium)tetrakis-(2,3,4,6-tetrafluorophenyl)borate,
tropillium tetrakis-(2,3,4,6-tetrafluorophenyl)borate,
triphenylcarbenium tetrakis-(2,3,4,6-tetrafluorophenyl)borate,
triphenylphosphonium tetrakis-(2,3,4,6-tetrafluorophenyl)borate,
triethylsilylium tetrakis-(2,3,4,6-tetrafluorophenyl)borate,
benzene(diazonium)tetrakis-(2,3,4,6-tetrafluorophenyl)borate,
trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(t-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium)tetrakis(3,5-bis(trifluoromethyl)phenyl)borate,
tropillium tetrakis(3,5-bis(trifluoromethyl)phenyl)borate,
triphenylcarbenium tetrakis(3,5-bis(trifluoromethyl)phenyl)borate,
triphenylphosphonium tetrakis(3,5-bis(trifluoromethyl)phenyl)borate,
triethylsilylium tetrakis(3,5-bis(trifluoromethyl)phenyl)borate,
benzene(diazonium)tetrakis(3,5-bis(trifluoromethyl)phenyl)borate,
di-(i-propyl)ammonium tetrakis(pentafluorophenyl)borate,
dicyclohexylammonium tetrakis(pentafluorophenyl)borate,
tri(o-tolyl)phosphonium tetrakis(pentafluorophenyl)borate,
tri(2,6-dimethylphenyl)phosphonium tetrakis(pentafluorophenyl)borate,
triphenylcarbenium tetrakis(perfluorophenyl)borate,
1-(4-(tris(pentafluorophenyl)borate)-2,3,5,6-tetrafluorophenyl)pyrrolidinium,
tetrakis(pentafluorophenyl)borate,
4-(tris(pentafluorophenyl)borate)-2,3,5,6-tetrafluoropyridine, and
triphenylcarbenium tetrakis(3,5-bis(trifluoromethyl)phenyl)borate).

18. The catalyst system of claim 11, wherein the catalyst system is supported.

19. The catalyst system of claim 18, wherein the catalyst system is supported on silica.

20. A process to polymerize olefins comprising contacting one or more olefins with a catalyst system comprising an activator and a catalyst compound of claim 1.

21. The process of claim 20, wherein the process occurs at a temperature of from about 0° C. to about 300° C., at a pressure in the range of from about 0.35 MPa to about 10 MPa, and at a time up to 300 minutes.

22. The process of claim 20 further comprising obtaining polymer.

23. The metallocene catalyst compound of claim 2, wherein $R^2$ is an isopropyl, sec-butyl, 1-methylbutyl, 1-ethylpropyl, 1-methylpentyl, 1-ethylbutyl, 1-methylhexyl, 1-ethylpentyl, or 1-propylbutyl.

24. A metallocene catalyst compound represented by the formula:

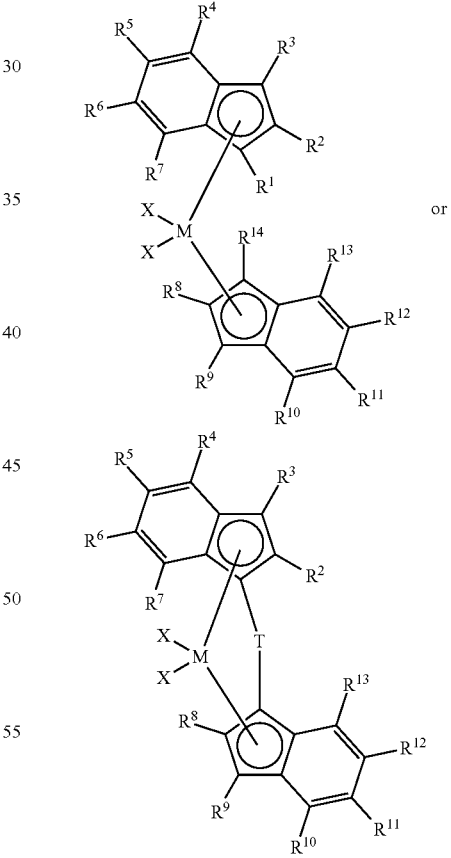

$R^2$ and $R^8$ are not the same;
$R^4$ and $R^{10}$ are substituted phenyl groups, where: both of $R^4$ and $R^{10}$ are a phenyl group substituted at the 3 and 5 positions, or one of $R^4$ and $R^{10}$ is a phenyl group substituted at the 3 and 5 positions and the other is a phenyl group substituted at the 2 position with an aryl group;

M is a group transition 2, 3 or 4 metal;
T is a bridging group;
each X is an anionic leaving group;
each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;
$R^2$ is selected from sec-butyl, 1-methylbutyl, 1-ethylpropyl, 1-methylpentyl, 1-ethylbutyl, 1-methylhexyl, 1-ethylpentyl, 1-propylbutyl; and
$R^8$ is a linear $C_1$-$C_{10}$ alkyl group which is optionally halogenated, wherein the metallocene catalyst compound is a mixture of rac/meso isomers and the rac/meso ratio is 10:1 or greater.

25. A metallocene catalyst compound represented by the formula:

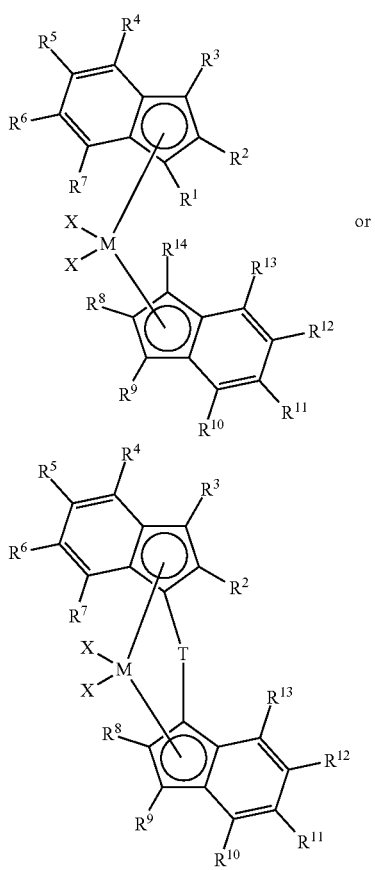

or $R^2$ and $R^8$ are not the same;
$R^4$ and $R^{10}$ are substituted phenyl groups, where: both of $R^4$ and $R^{10}$ are a phenyl group substituted at the 3 and 5 positions, or one of $R^4$ and $R^{10}$ is a phenyl group substituted at the 3 and 5 positions and the other is a phenyl group substituted at the 2 position with an aryl group;
M is a group transition 2, 3 or 4 metal;
T is a bridging group;
each X is an anionic leaving group;
each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;
$R^2$ is a substituted or unsubstituted $C_3$-$C_{20}$ hydrocarbyl group, where the group is substituted at the alpha position; and
$R^8$ is a butyl, pentyl, hexyl, heptyl, octyl, nonyl or decyl which is optionally halogenated.

26. A metallocene catalyst compound represented by the formula:

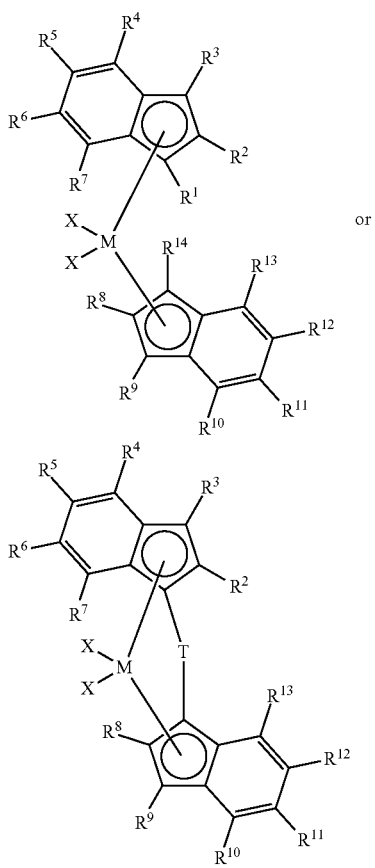

or $R^2$ and $R^8$ are not the same;
$R^4$ and $R^{10}$ are substituted phenyl groups, where: both of $R^4$ and $R^{10}$ are a phenyl group substituted at the 3 and 5 positions, or one of $R^4$ and $R^{10}$ is a phenyl group substituted at the 3 and 5 positions and the other is a phenyl group substituted at the 2 position with an aryl group;
M is a group transition 2, 3 or 4 metal;
T is a bridging group;
each X is an anionic leaving group;
each $R^1$, $R^3$, $R^5$, $R^6$, $R^7$, $R^9$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;
$R^2$ is sec-butyl, 1-methylbutyl, 1-ethylpropyl, 1-methylpentyl, 1-ethylbutyl, 1-methylhexyl, 1-ethylpentyl, 1-propylbutyl; and
$R^8$ is butyl, pentyl, hexyl, heptyl, octyl, nonyl or decyl) which is optionally halogenated, preferably with I, F, Cl or Br, wherein the metallocene catalyst compound is a mixture of rac/meso isomers and the rac/meso ratio is 10:1 or greater.

27. A metallocene catalyst compound represented by the formula:

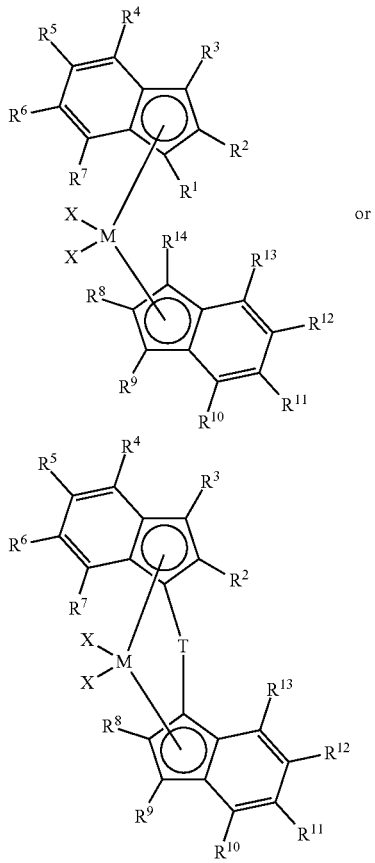

$R^2$ and $R^8$ are not the same;
$R^4$ and $R^{10}$ are substituted phenyl groups, where: both of $R^4$ and $R^{10}$ are a phenyl group substituted at the 3 and 5 positions, or one of $R^4$ and $R^{10}$ is a phenyl group substituted at the 3 and 5 positions and the other is a phenyl group substituted at the 2 position with an aryl group;
M is a group transition 2, 3 or 4 metal;
T is a bridging group;
each X is an anionic leaving group;
each $R^1$, $R^5$, $R^6$, $R^7$, $R^{11}$, $R^{12}$, $R^{13}$, and $R^{14}$ is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents;
$R^2$ is a substituted or unsubstituted $C_3$-$C_{20}$ hydrocarbyl group, where the group is substituted at the alpha position;
$R^8$ is a linear $C_1$-$C_{10}$ alkyl group which is optionally halogenated; and
$R^3$ and $R^9$ are independently selected from hydrogen or all isomers of butyl, pentyl, hexyl, heptyl, octyl, nonyl, decyl, undecyl, dodecyl, propenyl, butenyl, and from halocarbyls and all isomers of halocarbyls including perfluoropropyl, perfluorobutyl, perfluoroethyl, perfluoromethyl, and from substituted hydrocarbyl radicals and all isomers of substituted hydrocarbyl radicals including trimethylsilylpropyl, trimethylsilylmethyl, trimethylsilylethyl, and from phenyl, and all isomers of hydrocarbyl substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, dipropylmethylphenyl, and the like; from all isomers of halo substituted phenyl (where halo is, independently, fluoro, chloro, bromo and iodo) including halophenyl, dihalophenyl, trihalophenyl, tetrahalophenyl, and pentahalophenyl; and from all isomers of halo substituted hydrocarbyl substituted phenyl (where halo is, independently, fluoro, chloro, bromo and iodo) including halomethylphenyl, dihalomethylphenyl, (trifluoromethyl)phenyl, bis(triflouromethyl)phenyl; and from all isomers of benzyl, and all isomers of hydrocarbyl substituted benzyl including methylbenzyl, and dimethylbenzyl,
wherein the metallocene catalyst compound is a mixture of rac/meso isomers and the rac/meso ratio is 10:1 or greater.

28. The metallocene catalyst compound of claim 1, wherein the catalyst compound is supported.

29. The metallocene catalyst compound of claim 28, wherein $R^2$ is an alkyl group which is branched in a-position.

30. The metallocene catalyst compound of claim 28, wherein $R^8$ is methyl, ethyl, propyl, butyl, pentyl, hexyl, heptyl, octyl, nonyl or decyl and the 3 and 5 positions are substituted with $C_1$ to $C_{10}$ alkyl groups or aryl groups or combinations thereof.

31. The metallocene catalyst compound of claim 28, wherein $R^8$ is methyl, ethyl, propyl, butyl, pentyl, hexyl, heptyl, octyl, nonyl or decyl and the 3 and 5 positions are substituted with $C_1$ to $C_{10}$ alkyl groups or aryl groups or combinations thereof.

32. The metallocene catalyst compound of claim 28, wherein M is Zr; $R^8$ is methyl, ethyl, propyl, butyl, pentyl, hexyl, heptyl, octyl, nonyl or decyl; T is $CH_2$, $CH_2CH_2$, $C(CH_3)_2$, $SiMe_2$, $SiPh_2$, $SiMePh$, $Si(CH_2)_3$, $Si(CH_2)_4$, $Si(Me_3SiPh)_2$, or $Si(CH_2)_5$; and $R^4$ and $R^{10}$ are independently a phenyl group substituted at the 3 and 5 positions, where the 3 and 5 positions are substituted with $C_1$ to $C_{10}$ alkyl groups or aryl groups or combinations thereof.

33. The metallocene catalyst compound of claim 28, wherein the metallocene catalyst compound is a mixture of rac/meso isomers and the rac/meso ratio is 40:1.

34. The metallocene catalyst compound of claim 28, wherein at least one of $R^4$ and $R^{10}$ is a phenyl group substituted at the 3 and 5 positions with an aryl group.

35. The metallocene catalyst compound of claim 28, wherein at least one of $R^4$ and $R^{10}$ is an aryl group substituted at 3 and 5 positions with $C_1$ to a $C_{10}$ alkyl groups.

36. The metallocene catalyst compound of claim 28, wherein the 3 and 5 positions are substituted with t-butyl, sec-butyl, n-butyl, isopropyl, n-propyl, cyclopropyl, cyclobutyl, cyclopentyl, cyclohexyl, cycloheptyl, cyclooctyl, phenyl, mesityl, or adamantyl, or aryl groups and combinations thereof, wherein, when $R^4$ or $R^{10}$ is a phenyl group which is further substituted with an aryl group, the two groups bound together can be joined together directly or by linker groups, wherein the linker group is an alkyl, vinyl, phenyl, alkynyl, silyl, germyl, amine, ammonium, phosphine, phosphonium, ether, thioether, borane, borate, alane or aluminate group.

37. The metallocene catalyst compound of claim 1, wherein the 2 position is substituted with a substituted phenyl group.

38. The metallocene catalyst compound of claim 1, wherein the 2 position is substituted with a phenyl group.

* * * * *